United States Patent
Igarashi et al.

(10) Patent No.: US 6,310,231 B1
(45) Date of Patent: Oct. 30, 2001

(54) PARTICULAR SILANE COMPOUNDS, LUMINESCENT DEVICE MATERIALS COMPRISING SAID COMPOUNDS, AND LUMINESCENT DEVICES CONTAINING SAID MATERIALS

(75) Inventors: Tatsuya Igarashi; Toshiki Taguchi, both of Kanagawa (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/543,749

(22) Filed: Apr. 5, 2000

(30) Foreign Application Priority Data

Apr. 7, 1999 (JP) .................................. 11-100416
Mar. 14, 2000 (JP) .................................. 12-70609

(51) Int. Cl.[7] .............................. C07F 7/08; H05B 33/00; H05B 33/12; H05B 33/14
(52) U.S. Cl. ..................... 556/489; 556/430; 556/431; 556/549; 556/4; 556/214; 556/546; 556/14; 556/548; 556/110; 556/544; 556/229; 556/428; 556/690; 556/212; 556/917; 313/504; 313/506
(58) Field of Search .................. 556/430, 431, 556/489; 549/4, 214; 546/14; 548/110; 544/229; 428/690, 212, 917; 313/504, 506

(56) References Cited

U.S. PATENT DOCUMENTS

| | | | |
|---|---|---|---|
| 5,432,014 | * 7/1995 | Sano et al. ............................ | 428/690 |
| 5,449,564 | * 9/1995 | Nishio et al. ......................... | 428/690 |
| 5,529,853 | * 6/1996 | Hamada et al. ...................... | 428/690 |
| 5,601,903 | * 2/1997 | Fujii et al. .......................... | 428/690 X |
| 5,674,597 | * 10/1997 | Fujii et al. .......................... | 428/690 X |
| 5,792,557 | * 8/1998 | Nakaya et al. ....................... | 428/690 X |
| 5,830,972 | * 11/1998 | Ueda et al. .......................... | 556/430 X |
| 5,837,391 | * 11/1998 | Utsugi ................................ | 428/690 |
| 5,858,564 | * 1/1999 | Tamura et al. ....................... | 428/690 |
| 5,861,469 | * 1/1999 | Auner et al. ........................ | 556/431 X |
| 5,965,684 | * 1/1999 | Auner et al. ........................ | 556/431 X |
| 6,066,712 | * 5/2000 | Yeda et al. .......................... | 556/431 X |
| 6,165,383 | * 12/2000 | Chou ................................... | 556/431 X |
| 6,232,001 | * 5/2001 | Igarashi .............................. | 428/690 |

FOREIGN PATENT DOCUMENTS

| | | |
|---|---|---|
| 6-234968 | 8/1994 | (JP) . |
| 9-255949 | 9/1997 | (JP) . |
| 10-265773 | 10/1998 | (JP) . |
| 11-3781 | 1/1999 | (JP) . |

* cited by examiner

*Primary Examiner*—Paul F. Shaver
(74) *Attorney, Agent, or Firm*—Sughrue, Mion, Zinn, Macpeak & Seas, PLLC

(57) ABSTRACT

Silane compounds as a constituent material of luminescent device are described, which are represented by formula (1), luminescent device materials which comprise said compounds and luminescent devices which comprise said materials to acquire high luminous efficiency and high durability:

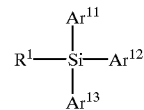

(1)

wherein $R^1$ represents an alkyl group, an aryl group, a heteroaryl group or an alkynyl group, and each of $Ar^{11}$, $Ar^{12}$ and $Ar^{13}$ represents a heteroaryl group.

20 Claims, No Drawings

PARTICULAR SILANE COMPOUNDS, LUMINESCENT DEVICE MATERIALS COMPRISING SAID COMPOUNDS, AND LUMINESCENT DEVICES CONTAINING SAID MATERIALS

FIELD OF THE INVENTION

The present invention relates to particular silane compounds, luminescent device materials comprising such compounds, and luminescent devices containing such materials. BACKGROUND OF THE INVENTION Nowadays various display devices (organic luminescent devices) utilizing organic fluorescent materials are researched and developed energetically. Of these devices, the organic electroluminescent (EL) devices are promising display devices that deserve special attention because they can emit light of high luminance under a low applied voltage. For instance, the EL devices of a type which comprises organic thin layers formed by evaporating organic compounds are known (*Applied Physics Letters*, vol.51, p.913 (1987)). More specifically, such a type of organic EL devices have a laminated structure made up of an electron transfer material and a hole transfer material, and their luminous characteristics show substantial improvements over those of conventional devices of single-layer type.

With the reports printed in the journal cited above, the study and development of organic EL devices have been made lively. And various electron transfer materials and hole transfer materials have been developed and examined for the purpose of enhancing luminous efficiency. As to the electron transfer materials, however, no compounds superior in properties to tris (8-hydroxyquinolinato) aluminum (usually abbreviated as "Alq") have yet been found. Such being the case, it has been desired to develop compounds capable of surpassing Alq in properties. In addition, Alq fluoresces a green color, so that it has no suitability as an electron transfer material for blue luminescent devices. Therefore, it has been desired to find out electron transfer materials suitable for blue luminescent devices.

Also, the application of organic EL devices to full color display has been actively examined in recent years. In order to develop a high-performance full color display, it is necessary to heighten the color purity of each of blue luminescence, green luminescence and red luminescence. However, the luminescence of high color purity is difficult to obtain. For instance, the distyrylarylene compounds (DPVBi) described in a book, entitled *Yuki EL Soshi to sono Kogyoka Saizensen* (which means "Organic EL devices and the forefront of their industialization"), page. 38, published by N.T.S. Co., and Zn(OXZ)$_2$ (benzene ring-condensed nitrogen-containing heterocyclic compounds) described in the book, supra, page 40, and JP-A-7-133483 (the term "JP-A" as used herein means an "unexamined published Japanese patent application") are blue luminescent materials which have undergone extensive examinations, but they can merely provide blue luminescence of low color purity. Therefore, there is plenty of room for improvement.

Another important characteristic that is required for organic EL device materials is durability. In particular, the amorphous film stability constitutes an important factor in the enhancement of durability. Therefore, it has been expected to develop compounds usable as organic EL device materials and capable of forming highly stable amorphous films. For instance, N,N'-diphenyl-N,N'-di(m-tolyl) benzidine (TPD) is an extensively utilized hole transfer material and has high hole transfer capacity. Although the TPD evaporated film can be present in a uniform amorphous state for a short while after the evaporation was finished, cases occurs in which the TPD evaporated film crystallizes after a lapse of several hours have passed from the evaporation. In such cases, the durability of EL devices is greatly lowered.

SUMMARY OF THE INVENTION

An object of the present invention is to develop an organic luminescent device material which can ensure high luminous efficiency and high durability in the luminescent device, and to provide a luminescent device using such a material.

The aforementioned object is attained in accordance with the following Embodiments (1) to (9).

(1) A luminescent device material, with the material comprising a compound represented by the following formula (1)

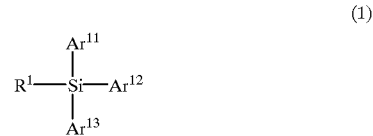

wherein $R^1$ represents an alkyl group, an aryl group, a heteroaryl group or an alkynyl group, and each of $Ar^{11}$, $Ar^{12}$ and $Ar^{13}$ represents a heteroaryl group.

(2) A luminescent device material, with the material comprising a compound represented by the following formula (2):

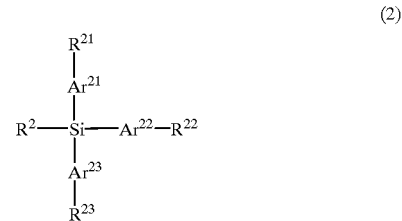

wherein $R^2$ represents an alkyl group, an aryl group, a heteroaryl group or an alkynyl group, each of $Ar^{21}$, $Ar^{22}$ and $Ar^{23}$ represents an arylene group, and each of $R^{21}$, $R^{22}$ and $R^{23}$ represents an aryl group or a heteroaryl group.

(3) A luminescent device material, with the material comprising a compound represented by the following formula (3)

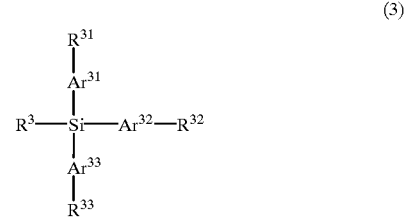

wherein $R^3$ represents an alkyl group, an aryl group, a heteroaryl group or an alkynyl group, each of $Ar^{31}$, $Ar^{32}$ and $Ar^{33}$ represents an arylene group, and each of $R^{31}$, $R^{32}$ and $R^{33}$ represents an alkenyl group or an alkynyl group.

(4) A luminescent device material, with the material comprising a compound represented by the following formula (4):

(4)

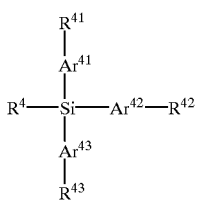

wherein $R^4$ represents an alkyl group, an aryl group, a heteroaryl group or an alkynyl group, each of $Ar^{41}$, $Ar^{42}$ and $Ar^{43}$ represents an arylene group, each of $R^{41}$, $R^{42}$ and $R^{43}$ represents $-NR^{44}R^{45}$, $-OR^{46}$ or $-S-R^{47}$, and each of $R^{44}$, $R^{45}$, $R^{46}$ and $R^{47}$ represents a hydrogen atom or a substituent group.

(5) A luminescent device material, with the material comprising a compound represented by the following formula (5)

(5)

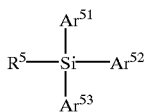

wherein $R^5$ represents an alkyl group, an aryl group, a heteroaryl group or an alkynyl group, and each of $Ar^{51}$, $Ar^{52}$ and $Ar^{53}$ represents a group containing at least three aromatic hydrocarbon rings in a condensed state.

(6) A compound represented by the following formula (6):

(6)

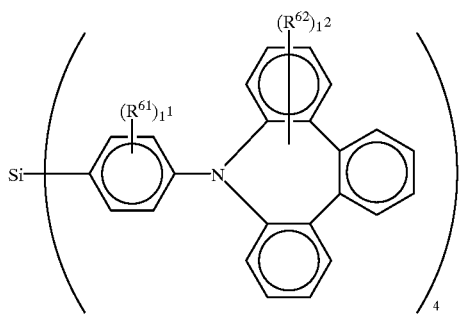

wherein each of $R^{61}$ and $R^{62}$ represents a substituent group, $l^1$ represents an integer of 0 to 4, and $l^2$ represents an integer of 0 to 12.

(7) A compound representedby the following formula (7):

(7)

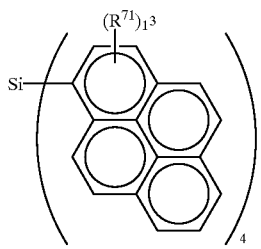

wherein $R^{71}$ represents a substituent group, and $l^1$ represents an integer of 0 to 9.

(8) A compound represented by the following formula (8)

(8)

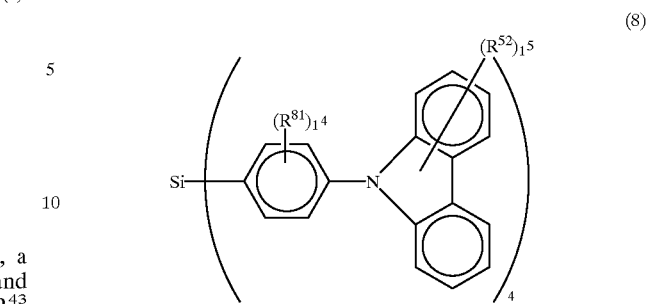

wherein each of $R^{81}$ and $R^{82}$ represents a substituent group, $l^4$ represents an integer of 0 to 4, and $i^5$ represents an integer of 0 to 8.

(9) A luminescent device containing at least one among the compounds represented by the formulae (1), (2), (3), (4), (5), (6), (7) and (8) defined in Embodiments (1), (2), (3), (4) (5), (6), (7) and (8) respectively.

DETAILED DESCRIPTION OF THE INVENTION

The compounds of the present invention (namely the compounds represented by formulae (1), (2), (3), (4), (5), (6), (7) and (8) respectively) are described below in detail.

First, the groups constituting the formula (1) are illustrated.

$R^1$ represents an alkyl group (containing preferably 1 to 20, more preferably 1 to 12, particularly preferably 1 to 8, carbon atoms, with examples including methyl, ethyl, isopropyl, tert-butyl, n-octyl, n-decyl, n-hexadecyl, cyclopropyl, cyclopentyl and cyclohexyl groups), an aryl group (containing preferably 6 to 30, more preferably 6 to 20, particularly preferably 6 to 12, carbon atoms, with examples including phenyl, p-methylphenyl and naphthyl groups), a heteroaryl group (containing preferably 1 to 50, more preferably 1 to 30, particularly preferably 2 to 12, carbon atoms in addition to any of oxygen, sulfur and nitrogen atoms, with examples including imidazolyl, pyridyl, furyl, piperidyl, benzoxazolyl, thienyl, triazolyl and carbazolyl groups), or an alkynyl group (containing preferably 2 to 20, more preferably 2 to 12, particularly preferably 2 to 8, carbon atoms, with examples including propargyl and 2-pentynyl groups). These groups may further be substituted.

It is desirable for $R^1$ to be an alkyl group, an aryl group or a heteroaryl group, more preferably an aryl group or a heteroaryl group, further preferably a heteroaryl group, particularly preferably $-Ar^{14}$ group (wherein $Ar^{14}$ has the same meaning as $A^{11}$ described below).

$Ar^{11}$, $Ar^{12}$ and $Ar^{13}$ each represents a heteroaryl group. When the heteroaryl group is a group formed by condensing two or more rings (a condensed-ring heteroaryl group), it is desirable that the silicon atom be attached to the ring containing a hetero atom. Examples of a heteroaryl group preferred as each of $Ar^{11}$, $Ar^{12}$ and $Ar^{13}$ include a pyridyl group, a pyrazinyl group, an oxadiazolyl group, a triazolyl group, a thiadiazolyl group, a thienyl group, a carbazolyl group, a quinolino group, a benzazolyl group (such as a benzoxazolyl, benzimidazolyl or benzothiazolyl group, preferably a benzoxazolyl or benzimidazolyl group, more preferably a benzimidazolyl group) and a carbazolyl group. Of these groups, pyridyl, pyrazinyl, oxadiazolyl, triazolyl, quinolino, benzazolyl and carbazolyl groups are preferred over the others. Further, pyridyl, pyrazinyl, benzazolyl and carbazolyl groups, particularly pyridyl, benzazolyl and carbazolyl groups, are preferred over the others. The substituent groups which may be present on the heteroaryl groups as described above include the groups described above as $R^1$, the groups described below as $R^{21}$, $R^{31}$ and $R^{41}$ respectively, and a cyano group. Of these groups, the groups described below as $R^{21}$, $R^{31}$ and $R^{41}$ respectively are preferred over the others.

Secondly, the groups constituting the formula (2) are illustrated below.

$R^2$ represents an alkyl group (containing preferably 1 to 20, more preferably 1 to 12, particularly preferably 1 to 8, carbon atoms, with examples including methyl, ethyl, isopropyl, tert-butyl, n-octyl, n-decyl, n-hexadecyl, cyclopropyl, cyclopentyl and cyclohexyl groups), an aryl group (containing preferably 6 to 30, more preferably 6 to 20, particularly preferably 6 to 12, carbon atoms, with examples including phenyl, p-methylphenyl and naphthyl groups), a heteroaryl group (containing preferably 1 to 50, more preferably 1 to 30, particularly preferably 2 to 12, carbon atoms in addition to any of oxygen, sulfur and nitrogen atoms, with examples including imidazolyl, pyridyl, furyl, piperidyl, benzoxazolyl, thienyl, triazolyl and carbazolyl groups), or an alkynyl group (containing preferably 2 to 20, more preferably 2 to 12, particularly preferably 2 to 8, carbon atoms, with examples including propargyl and 3-pentynyl groups). These groups may further be substituted.

It is desirable for $R^2$ to be an alkyl group, an aryl group or a heteroaryl group, more preferably an aryl group or a heteroaryl group, further preferably an aryl group, particularly preferably —$Ar^{24}$—$R^{24}$ group (wherein $Ar^{24}$ and $R^{24}$ have the same meaning as the following $Ar^{21}$ and $R^{21}$, respectively).

$Ar^{21}$, $Ar^{22}$ and $Ar^{23}$ each represents an arylene group (containing preferably 6 to 40, more preferably 6 to 30, further preferably 6 to 12, carbon atoms). It is desirable for each of $Ar^{21}$, $Ar^{22}$ and $Ar^{23}$ to be a phenylene group, a naphthylene group, an anthrylene group, a pyrenylene group or a rubrenylene group, more preferably a phenylene group, a naphthylene group or an anthrylene group, further preferably a phenylene group, particularly preferably an unsubstituted p-phenylene group.

$R^{21}$, $R^{22}$ and $R^{22}$ each represents an aryl group (preferably a phenyl group, a naphthyl group or the group containing at least three aromatic hydrocarbon rings in a condensed state (examples of which include the groups hereinafter described as $Ar^{51}$), more preferably the group containing at least three aromatic hydrocarbon rings in a condensed state) or a heteroaryl group (preferably a pyridyl group, a pyrazinyl group, an oxadiazolyl group, a triazolyl group, a thiadiazolyl group, a thienyl group, a carbazolyl group, a quinolyl group or a benzoazolyl group (which includes a benzoxazolyl group, benzimidazolyl group and a benzothiazolyl group, preferably a benzoxazolyl group and a benzimidazolyl group, more preferably a benzimidazolyl group), more preferably a pyridyl group, a pyrazinyl group, an oxadiazolyl group, a triazolyl group, a benzazolyl group or a carbazolyl group, further preferably a pyridyl group, a pyrazinyl group, a benzazolyl group or a carbazolyl group, particularly preferably a pyridyl group, a benzazolyl group or a carbazolyl group) Of these groups, the heteroaryl group or the group containing at least three aromatic hydrocarbon rings in a condensed state (examples of which include the groups herein after described as $Ar^{51}$, and which has the same preferable scope as $Ar^{51}$ especially the group containing at least three aromatic hydrocarbon rings in a condensed state, is preferred as each of $R^{21}$, $R^{22}$ and $R^{23}$.

Thirdly, the groups constituting the formula (3) are illustrated below.

$R^3$ represents an alkyl group (containing preferably 1 to 20, more preferably 1 to 12, particularly preferably 1 to 8, carbon atoms, with examples including methyl, ethyl, isopropyl, tert-butyl, n-octyl, n-decyl, n-hexadecyl, cyclopropyl, cyclopentyl and cyclohexyl groups), an aryl group (containing preferably 6 to 30, more preferably 6 to 20, particularly preferably 6 to 12, carbon atoms, with examples including phenyl, p-methylphenyl and naphthyl groups), a heteroaryl group (containing preferably 1 to 50, more preferably 1 to 30, particularly preferably 2 to 12, carbon atoms in addition to any of oxygen, sulfur and nitrogen atoms, with examples including imidazolyl, pyridyl, furyl, piperidyl, benzoxazolyl, thienyl, triazolyl and carbazolyl groups), or an alkynyl group (containing preferably 2 to 20, more preferably 2 to 12, particularly preferably 2 to 8, carbon atoms, with examples including propargyl and 3-pentynyl groups) These groups may further be substituted.

It is desirable for $R^3$ to be an alkyl group, an aryl group or a heteroaryl group, more preferably an aryl group or a heteroaryl group, further preferably an aryl group, particularly preferably —$Ar^{34}$—$R^{34}$ group (wherein $Ar^{34}$ and $R^{34}$ have the same meaning as the following $Ar^{31}$ and $R^{31}$, respectively).

$Ar^{31}$, and $Ar^{32}$ each has the same meaning as $Ar^{21}$ defined above.

$R^{31}$, $R^{32}$ and $R^{33}$ each represents an alkenyl group (which includes both substituted and unsubstituted alkenyl groups, containing preferably 2 to 30, more preferably 2 to 20, particularly preferably 2 to 10, carbon atoms in each group, with examples including substituted or unsubstituted vinyl, allyl, 2-butenyl and 3-pentenyl groups) or an alkynyl group (which includes both substituted and unsubstituted alkynyl groups, containing preferably 2 to 30, more preferably 2 to 20, particularly preferably 2 to 10, carbon atoms in each group, with examples including propargyl and 3-pentynyl groups). Of these groups, the alkenyl group is preferred as $R^{31}$, $R^{32}$ and $R^{33}$ each. The substituent present on such an alkenyl group is preferably an aryl group or a heteroaryl group, more preferably a heteroaryl group.

Further, the groups constituting the foregoing formula (4) are illustrated.

$R^4$ represents an alkyl group (containing preferably 1 to 20, more preferably 1 to 12, particularly preferably 1 to 8, carbon atoms, with examples including methyl, ethyl, isopropyl, tert-butyl, n-octyl, n-decyl, n-hexadecyl, cyclopropyl, cyclopentyl and cyclohexyl groups), an aryl group (containing preferably 6 to 30, more preferably 6 to 20, particularly preferably 6 to 12, carbon atoms, with examples including phenyl, p-methylphenyl and naphthyl groups), a heteroaryl group (containing preferably 1 to 50, more preferably 1 to 30, particularly preferably 2 to 12, carbon atoms in addition to any of oxygen, sulfur and nitrogen atoms, with examples including imidazolyl, pyridyl, furyl, piperidyl, benzoxazolyl, thienyl, triazolyl and carbazolyl groups), or an alkynyl group (containing preferably 2 to 20, more preferably 2 to 12, particularly preferably 2 to 8, carbon atoms, with examples including propargyl and 3-pentynyl groups). These groups may further be substituted.

It is desirable for $R^4$ to be an alkyl group, an aryl group or a heteroaryl group, more preferably an aryl group or a heteroaryl group, further preferably an aryl group, particularly preferably —$Ar^{44}$—$R^{48}$ group (wherein $Ar^{44}$ and $R^{48}$ have the same meaning as the following $Ar^{41}$ and $R^{41}$, respectively).

$Ar^{42}$, $Ar^{42}$ and $Ar^{43}$ each has the same meaning as $Ar^{21}$ defined above.

$R^{41}$, $R^{42}$ and $R^{43}$ each represents —$NR^{44}R^{45}$ group, —$OR^{46}$ group or —S—$R^{47}$ group. $R^{44}$, $R^{45}$, $R^{46}$ and $R^{47}$ each represents a hydrogen atom or a substituent group. $R^{44}$ and $R^{45}$ may combine to complete a ring structure (such as a carbazole or benzoazepine ring) It is desirable for $R^{44}$ and $R^{45}$ each to be an alkyl group (which contains preferably 1 to 20 carbon atoms, more preferably 1 to 12 carbon atoms, particularly preferably 1 to 8 carbon atoms) an aryl group (which contains preferably 6 to 30, more preferably 6 to 20, particularly preferably 6 to 12, carbon atoms) oraheteroaryl group (which contains preferably at least one oxygen, sulfur or nitrogen atom in addition to 1 to 50, preferably 1 to 30, particularly preferably 2 to 12, carbon atoms) . Of these groups, the aryl group is preferred as $R^{44}$ and $R^{45}$ each. In particular, it is advantageous that $R^{44}$ and $R^{45}$ be each a phenyl or naphthyl group or they combine to complete a carbazole orbenzoazepine ring, especially a benzoazepine ring. It is desirable for $R^{46}$ and $R^{47}$ each to be an alkyl group (which contains preferably 1 to 20, more preferably 1 to 12, particularly preferably 1 to 8, carbon atoms) or an aryl group (which contains preferably 6 to 30, more preferably 6 to 20, particularly preferably 6 to 12, carbon atoms) , preferably an alkyl group. The group preferred as $R^{41}$, $R^{42}$ and $R^{43}$ each is —$NR^{44}R^{45}$ group or —$OR^{46}$ group, particularly —$NR^{44}R^{45}$.

The description of formula (5) is as follows. $R^5$ represents an alkyl group (which contains preferably 1 to 20, more preferably 1 to 12, particularly preferably 1 to 8, carbon atoms, with examples including methyl, ethyl, iso-propyl, tert-butyl, n-octyl, n-decyl, n-hexadecyl, cyclopropyl, cyclopentyl and cyclohexyl groups), an aryl group (which contains preferably 6 to 30, more preferably 6 to 20, particularly preferably 6 to 12, carbon atoms, with examples including phenyl, p-methylphenyl and naphthyl groups), a heteroaryl group (which contains preferably at least one oxygen, sulfur or nitrogen atom in addition to 1 to 50, preferably 1 to 30, particularly preferably 2 to 12, carbon atoms, with examples including imidazolyl, pyridyl, furyl, piperidyl, benzoxazolyl, thienyl, triazolyl and carbazolyl groups) , or an alkynyl group (which contains preferably 2 to 20, more preferably 2 to 12, particularly preferably 2 to 8, carbon atoms, with examples including propargyl and 3-pentynyl groups) These groups each may further be substituted.

It is desirable for $R^5$ to be an alkyl, aryl or heteroaryl group, more preferably an aryl or heteroacryl group, further preferably an aryl group, particularly preferably —$Ar^{54}$ group (wherein $Ar^{54}$ has the same meaning as $Ar^{51}$ defined below)

$Ar^{51}$, $Ar^{52}$ and $Ar^{53}$ each represents a group containing at least three aromatic hydrocarbon rings in a condensed state. As examples of a structure containing at least three aromatic hydrocarbon rings in a condensed state which constitutes the group containing at least three aromatic hydrocarbon rings represented by $Ar^{51}$, $Ar^{52}$ and $Ar^{53}$, mention may be made of the structures described, e.g. in *Aldrich Structure Index*, edition of 1996–1997, pages 177–178, Aldrich Co., *Library of Rare Chemicals Structure Index*, edition of 1993, pages 165–168, Sigma-Aldrich Co., and *Yuki Kagaku Seikagaku Meimeiho* (which means "Nomenclature in Organic Chemistry and Biochemisty*), volume 1 (translated by Kazuo Hirayama), pages 21–28, Nankodo Co. (1988) More specifically, the foregoing structures include an anthracene structure, a phenanthrene structure, a pyrene structure, a triphenylene structure, a perylene structure, a fluorantene structure, an indacene structure, an acenaphthylene structure, a fluorene structure, a tetraphenylene structure, and the structures formed by fusing together any one of the structures described above and another ring (such as benzoanthracene, benzopyrene, pentacene, coronene and chrycene structures).

It is desirable for $Ar^{51}$, $Ar^{52}$ and $Ar^{53}$ each to be an anthryl group, a phenenthryl group, a pyrenyl group or perylenyl group, preferably a pyrenyl group.

The formulae (6) and (8) constitute a desirable range of formula (4), and the formula (6) constitutes a more desirable range of formula (4); while the formula (7) constitutes a desirable range of formula (5).

The formula (6) is illustrated below. $R^{61}$ and $R^{62}$ each represents a substituent group, $l^1$ represents an integer of 0 to 4, and $l^2$ represents an integer of 0 to 12. Examples of a substituent group suitable for $R^{61}$ and $R^{62}$ each include an alkyl group (which contains preferably 1 to 30, more preferably 1 to 20, particularly preferably 1 to 10, carbon atoms, with examples including methyl, ethyl, iso-propyl, tert-butyl, n-octyl, n-decyl, n-hexadecyl, cyclopropyl, cyclopentyl and cyclohexyl groups), an alkenyl group (which contains preferably 2 to 30, more preferably 2 to 20, particularly preferably 2 to 10, carbon atoms, with examples including vinyl, allyl, 2-butenyl and 3-pentenyl groups), an alkynyl group (which contains preferably 2 to 30, more preferably 2 to 20, particularly preferably 2 to 10, carbon atoms, with examples including propargyl and 3-pentynyl groups), an aryl group (which contains preferably 6 to 30, more preferably 6 to 20, particularly preferably 6 to 12, carbon atoms, with examples including phenyl, p-methylphenyl, naphthyl and anthranyl groups), an amino group (which contains preferably 0 to 30, more preferably 0 to 20, particularly preferably 0 to 10, carbon atoms, with examples including amino, methylamino, dimethylamino, diethylamino, dibenzylamino, diphenylamino and ditolylamino groups), an alkoxy group (which contains preferably 1 to 30, more prefereably 1 to 20, particularly preferably 1 to 10, carbon atoms, with examples including methoxy, ethoxy, butoxy and 2-ethylhexyloxy groups), an aryloxy group (which contains preferably 6 to 30, more preferably 6 to 20, particularly preferably 6 to 12, carbon atoms, with examples including phenyloxy, 1-naphthyloxy and 2-naphthyloxy groups), a heteroaryloxy group (which contains preferably 1 to 30, more preferably 1 to 20, particularly preferably 1 to 12, carbon atoms, with examples including pyridyloxy, pyrazinyloxy, pyrimidyloxy and quinolyloxy groups), an acyl group (which contains preferably 1 to 30, more preferably 1 to 20, particularly preferably 1 to 12, carbon atoms, with examples including acetyl, benzoyl, formyl and pivaloyl groups), an alkoxycarbonyl group (which contains preferably 2 to 30, more preferably 2 to 20, particularly preferably 2 to 12, carbon atoms, and includes a methoxycarbonyl group and an ethoxycarbonyl group as examples), an aryloxycarbonyl group (which contains preferably 7 to 30, more preferably 7 to 20, particularly preferably 7 to 12, carbon atoms, and includes a phenyloxycarbonyl group as an example) , an acyloxy group (which contains preferably 2 to 30, more preferably 2 to 20, particularly preferably 2 to 10, carbon atoms, and includes an acetoxy group and a benzoyloxy group as examples) , an acylamino group (which contains preferably 2 to 30, more preferably 2 to 20, particularly preferably 2 to 10, carbon atoms, and includes an acetylamino group and benzoylamino group as examples), an alkoxycarbonylamino group (which contains preferably 2 to 30, more preferably 2 to 20, particularly preferably 2 to 12, carbon atoms, and includes amethoxycarbonylamino group as an example) an aryloxycarbonylamino group (which contains preferably 7 to 30, more preferably 7 to 20, particularly preferably 7 to 12, carbon atoms, and includes a phenyloxycarbonylamino group as an example), a sulfonylamino group (which contains preferably 1 to 30, more preferably 1 to 20, particularly preferably 1 to 12, carbon atoms, and includes a methanesulfonylamino group and a benzenesulfonylamino group as examples), a sulfamoyl group (which contains preferably 0 to 30, more preferably 0 to 20, particularly preferably 0 to 12, carbon atoms, with examples including sulfamoyl, methylsulfamoyl, dimethylsulfamoyl and phenylsulfamoyl groups), a carbamoyl group (which contains preferably 1 to 30, more preferably 1 to 20, particularly preferably 1 to 12, carbon atoms, with examples including carbamoyl, methylcarbamoyl, diethylcarbamoyl and phenylcarbamoyl groups), an alkylthio group (which contains preferably 1 to 30, more preferably 1 to 20, particularly preferably 1 to 12, carbon atoms, and includes a methylthio group and an ethylthio group as examples), an arylthio group (which contains preferably 6 to 30, more preferably 6 to 20, particularly preferably 6 to 12, carbon atoms, and includes a phenylthio group as an example), a heteroarylthio group (which contains preferably 1 to 30, more preferably 1 to 20, particularly preferably 1 to 12, carbon atoms, with examples including pyridylthio, 2-benzimidazolylthio, 2-benzoxazolylthio and 2-benzothiazolylthio groups), a sulfonyl group (which contains preferably 1 to 30, more preferably 1 to 20, particularly preferably 1 to 12, carbon atoms, and includes a mesyl group and a tosyl group as examples), a sulfinyl group (which contains preferably 1 to 30, more preferably 1 to 20, particularly preferably 1 to 12, carbon atoms, and includes a methanesulfinyl group and a benzenesulfinyl group as examples) an ureido group (which contains preferably 1 to 30, more preferably 1 to 20, particularly preferably 1 to 12, carbon atoms, with examples including ureido, methylureido and phenylureido groups), a phosphonamido group (which contains preferably 1 to 30, more preferably 1 to 20, particularly preferably 1 to 12, carbon atoms, and includes a diethylphosphonamido group and a phenylphosphonamido group as examples) , a hydroxyl group, a mercapto group, a halogen atom (e.g., fluorine, chlorine, bromine, iodine), a cyano group, a sulfo group, a carboxyl group, a nitro group, a hydroxamic acid group, a sulfino group, a hydrozino group, an imino group, a heterocyclic group (which contains preferably 1 to 30, more preferably 1 to 12, carbon atoms in addition to at least one hetero atom, e.g., a nitrogen atom, an oxygen atom or a sulfur atom, with examples including imidazolyl, pyridyl, quinolyl, furyl, thienyl, piperidyl, morpholino, benzoxazolyl, benzimidazolyl, benzothiazolyl and carbazolyl groups) and a silyl group (which contains preferably 3 to 40, more preferably 3 to 30, particularly preferably 3 to 24, carbon atoms, and includes a trimethylsilyl group and a triphenylsilyl group as examples) These groups each may further be substituted, and they may combine in pairs to form a ring structure.

The group desirable for $R^{61}$ and $R^{62}$ each is an alkyl group, an aryl group or a heteroaryl group, especially an alkyl group or an aryl group. The integer desirable for $l^1$ is 0, 1 or 2, especially 0 or 1, and the integer desirable for $l^2$ is 0, 1, 2, 3 or 4, especially 0 or 1.

The description of formula (7) is as follows. $R^{71}$ represents a substituent group, and $l^3$ represents an integer of 0 to 9. Examples of such a substituent group include the same groups as described in the description of $R^{61}$. The substituent group desirable for $R^{71}$ is an alkyl group, an aryl group or a heteroaryl group, especially an alkyl or aryl group. The integer desirable for $l^3$ is 0, 1 or 2, especially 0 or 1.

The description of formula (8) is as follows. $R^{81}$ and $R^{82}$ each represents a substituent group, $l^4$ represents an integer of 0 to 4, and $l^5$ represents an integer of 0 to 8. Examples of such a substituent group include the same groups as described in the description of $R^{61}$. The substituent group desirable for $R^{81}$ and $R^{82}$ each is an alkyl group, an aryl group or a heteroaryl group, especially an alkyl or aryl group. The integer desirable for $l^4$ is 0, 1 or 2, especially 0 or 1. Also, the integer desirable for $l^5$ is 0, 1 or 2, especially 0 or 1.

The compound of the present invention may be the so-called low molecular weight compound containing only one skeleton of a silane compound represented by the formula (1), (2), (3), (4), (5), (6), (7) or (8), or may be a high molecular weight compound (polymer or oligomer) having as its side chains any skeletons of silane compounds represented by formulae (1) to (8) respectively (the weight average molecular weight (Mw) of which is preferably from 1,000 to 5,000,000, more preferably from 2,000 to 1,000,000, further preferably from 3,000 to 50,000) or a high molecular weight compound containing in its main chain any skeletons of silane compounds represented by formulae (1) to (8) respectively (the weight average molecular weight (Mw) of which is preferably from 1,000 to 5,000,000, more preferably from 2,000 to 1,000,000, particularly preferably from 3,000 to 500,000). These high molecular weight compounds each may be a homopolymer, a copolymer of at least two of the compounds represented by formulae (1) to (8) or a copolymer of any of the compounds represented by formulae (1) to (8) and other monomers.

It is desirable for the compound of the present invention to be a low molecular weight compound represented by any of the formulae (1) to (8), or a high molecular weight compound containing in its main chain the skeletons of any of silane compounds representedby the formulae (1) to (8). In particular, the low molecular weight compound is preferred as the compound of the present invention.

Examples of four types of silane compounds according to the present invention are illustrated below, but it should be understood that these examples are not to be construed as limiting the scope of the present invention in any way.

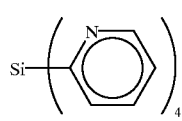

(1-1)

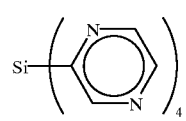

(1-2)

-continued
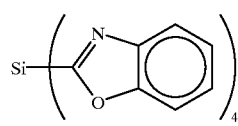
(1-3)
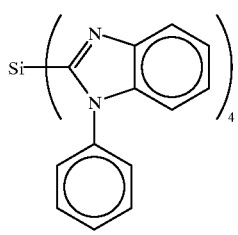
(1-4)
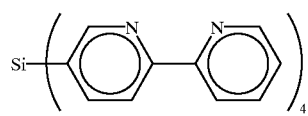
(1-5)
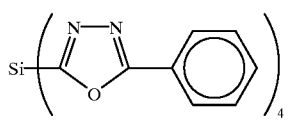
(1-6)
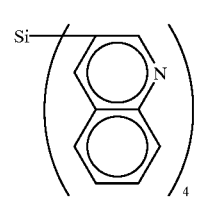
(1-7)
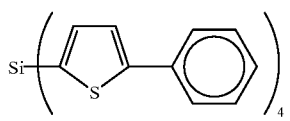
(1-8)
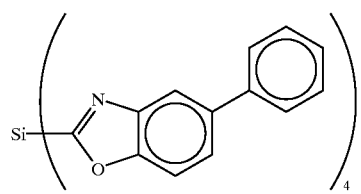
(1-9)
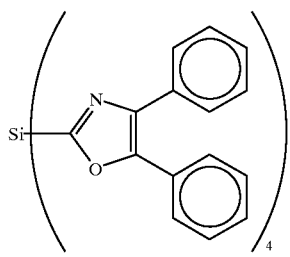
(1-10)
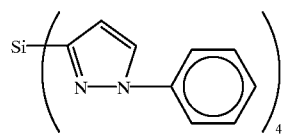
(1-11)
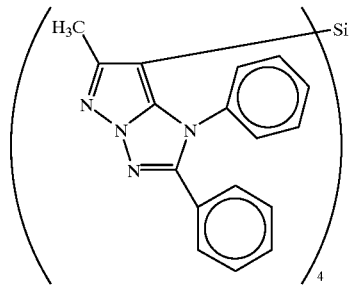
(1-12)
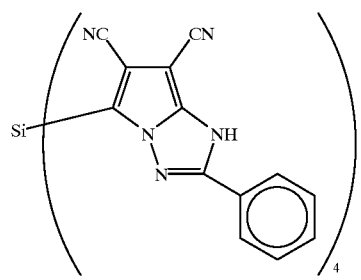
(1-13)
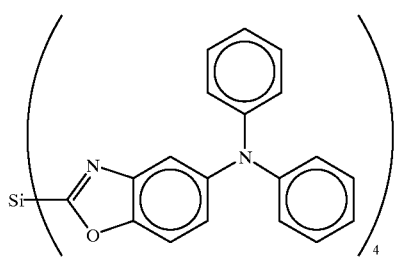
(1-14)

-continued
(1-15) 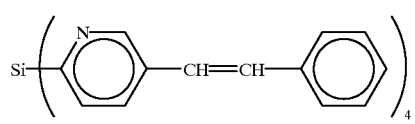
(1-16) 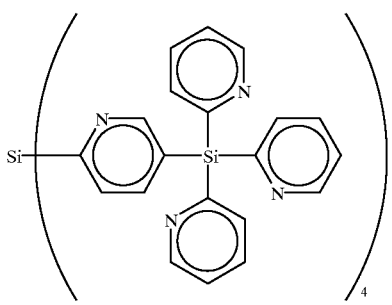
(1-17) 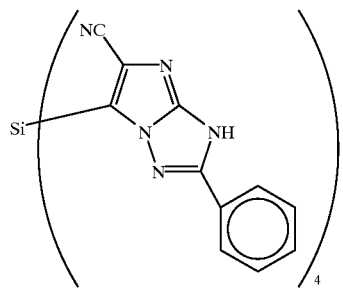
(1-18) 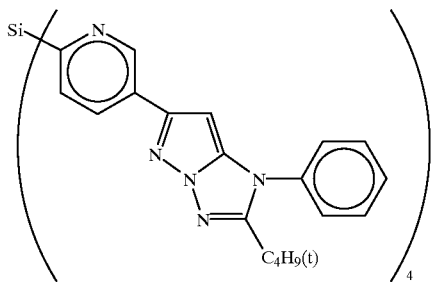
(1-19) 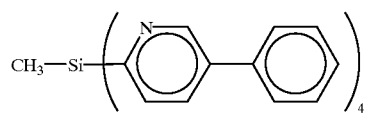
(1-20) 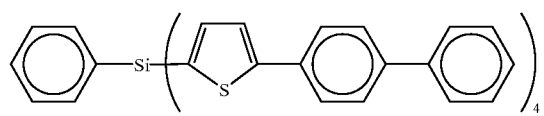
(1-21) 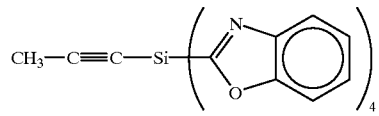
(1-22) 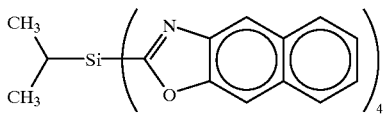
(1-23) 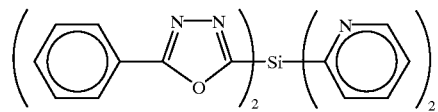
(1-24) 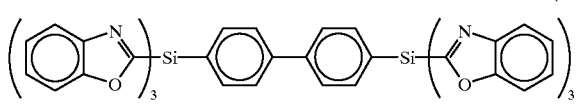
(1-25) 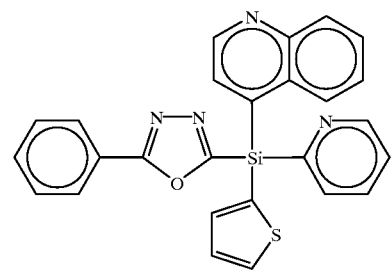
(1-26) 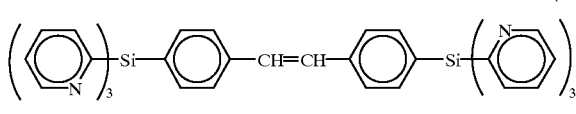
(1-27) 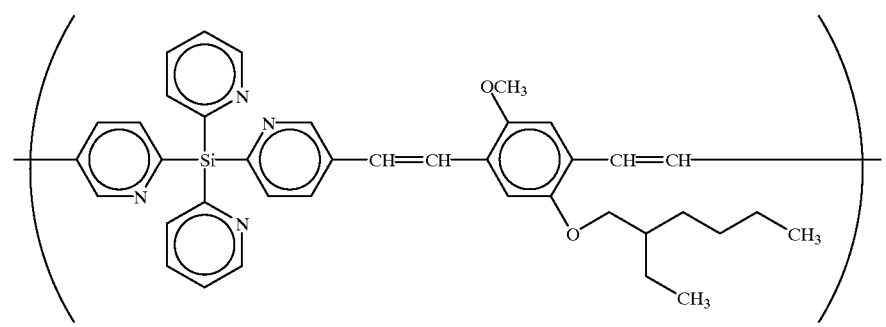

(1-28)
Weight average
molecular weight Mw = 12100
(converted to a polystyrene basis)
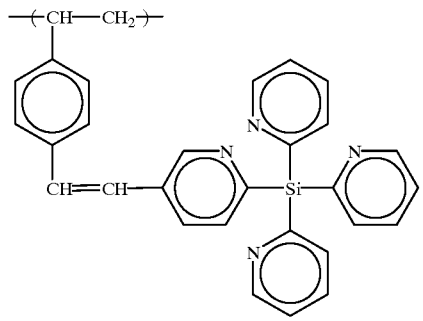
Mw = 3200
(converted to a polystyrene basis)
(1-29)
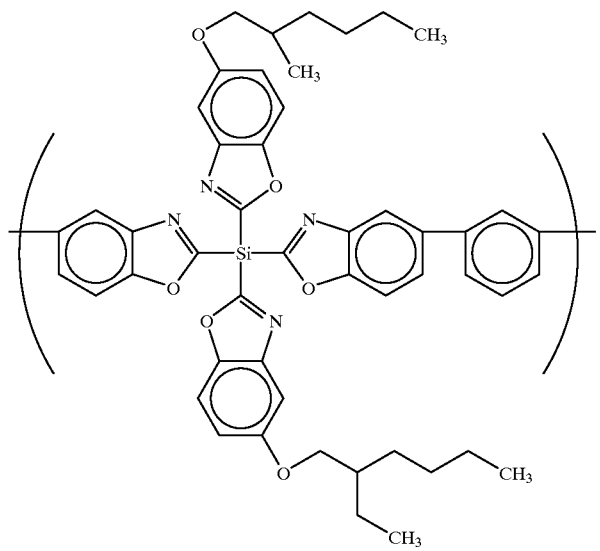
Mw = 4200
(converted to a polystyrene basis)
(1-30)
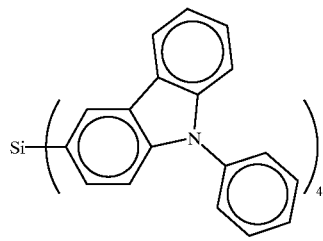
(2-1)
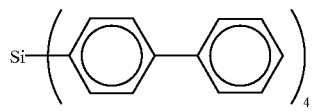
(2-2)
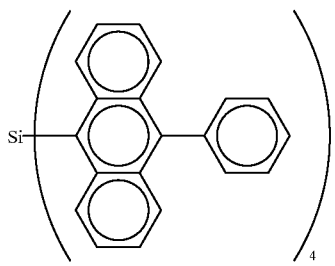

-continued
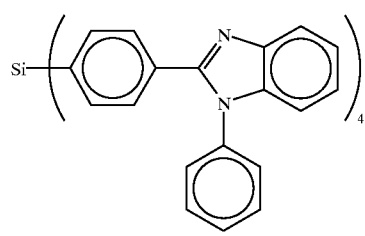
(2-3)
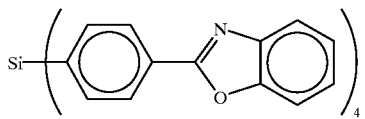
(2-4)
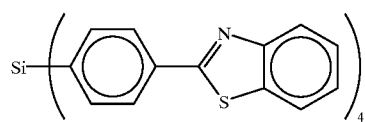
(2-5)
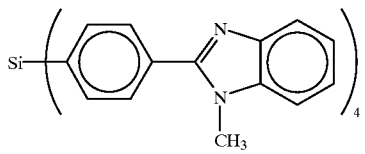
(2-6)
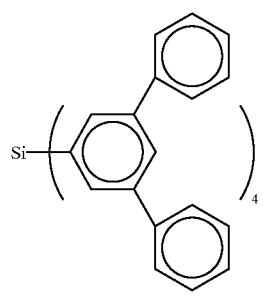
(2-7)
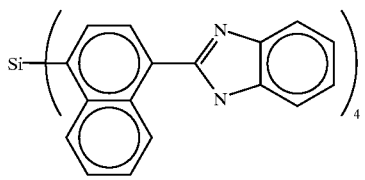
(2-8)
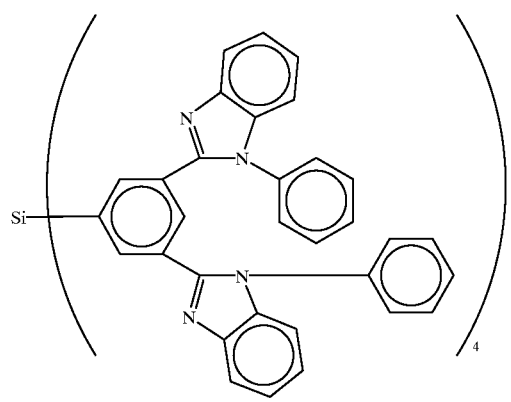
(2-9)
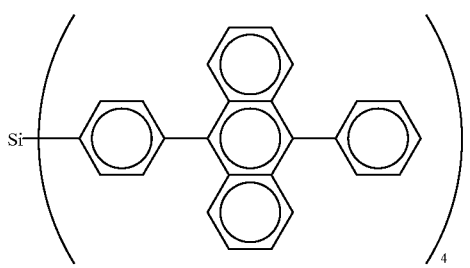
(2-10)
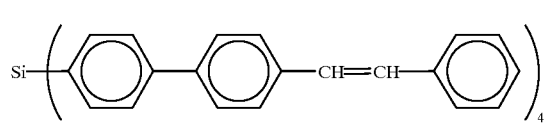
(2-11)
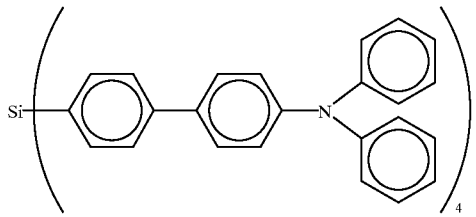
(2-12)
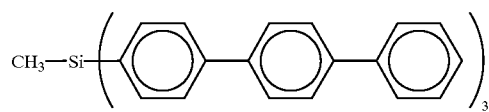
(2-13)
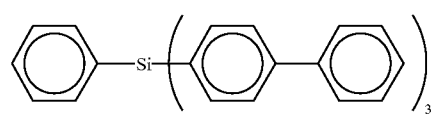
(2-14)

(2-15)
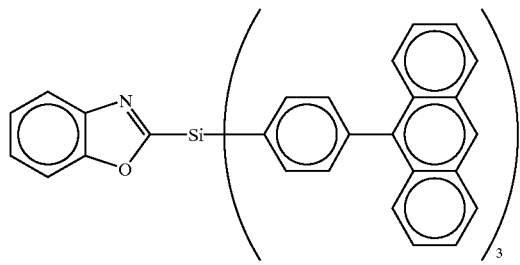
(2-16)
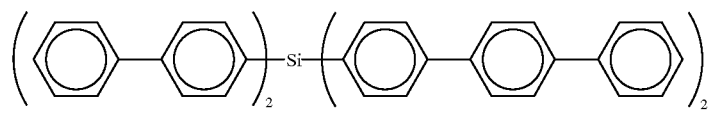
(2-17)
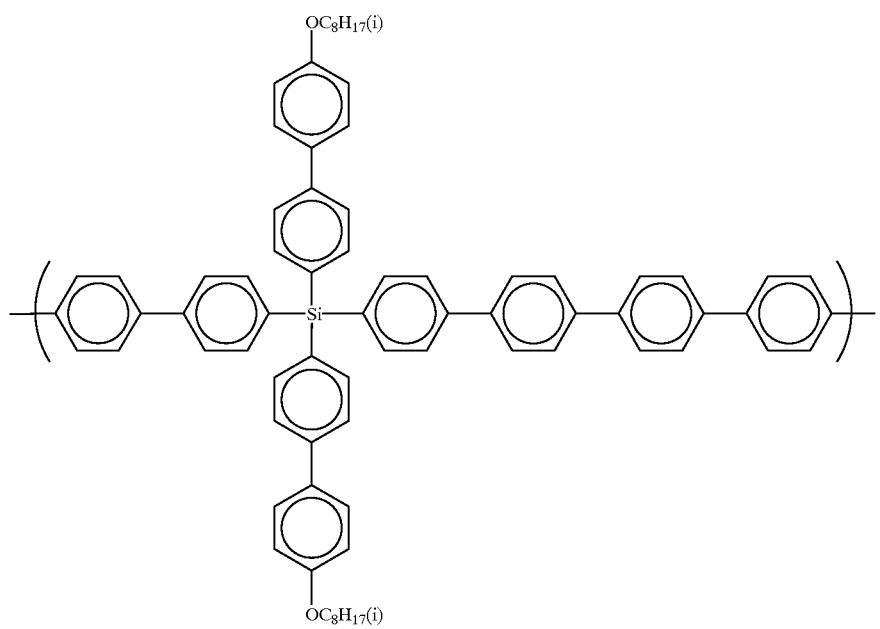
Mw = 9800 (converted to a polystyrene basis)
(2-18)
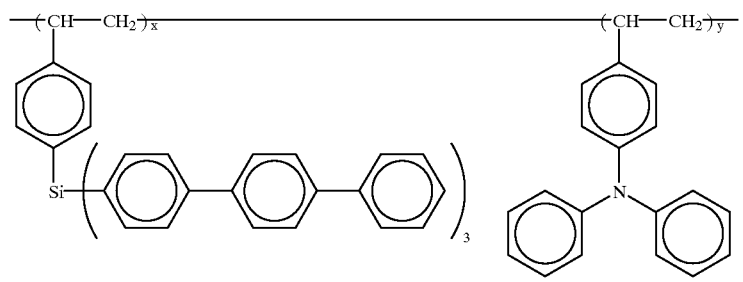
x/y = 1/9 (by weight)    Mw = 12200 (converted to a polystyrene basis)

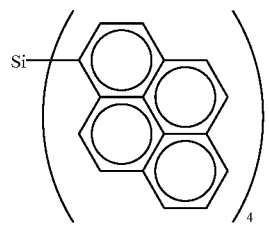
(2-19)
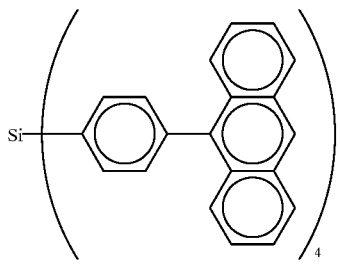
(2-20)
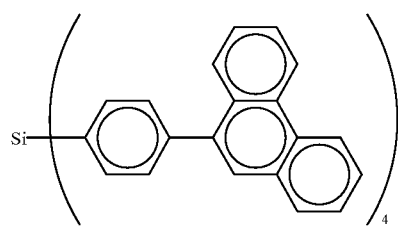
(2-21)
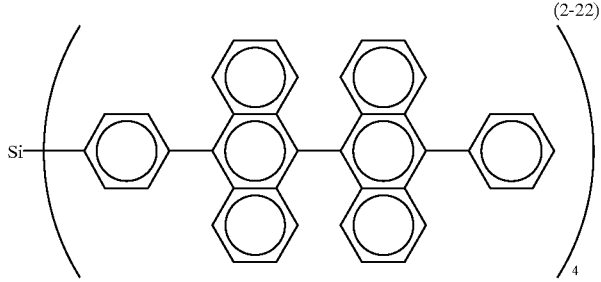
(2-22)
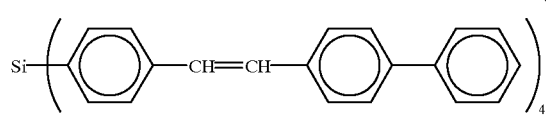
(3-1)
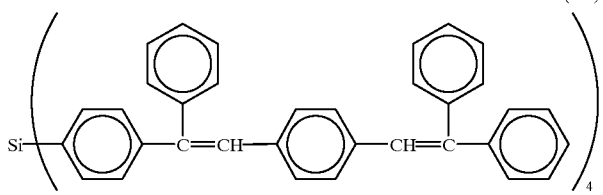
(3-2)
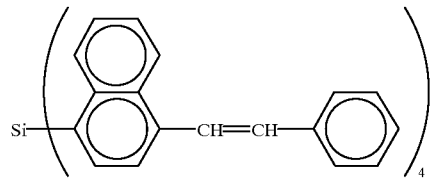
(3-3)
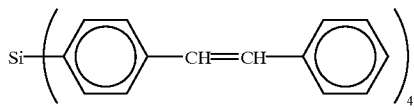
(3-4)
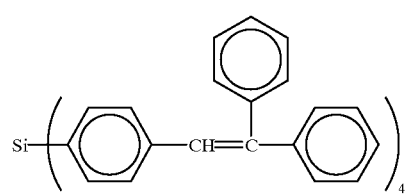
(3-5)
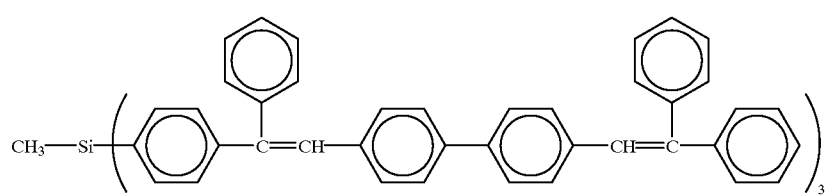
(3-6)

-continued
(3-7)
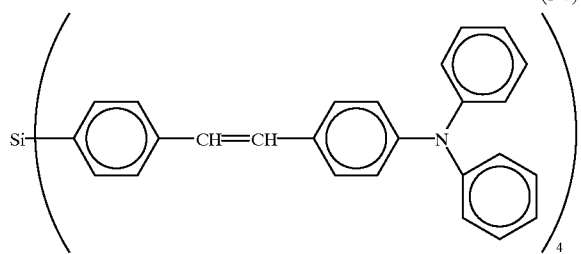
(3-8)
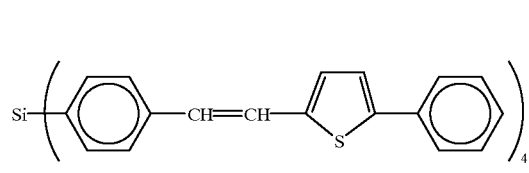
(3-9)
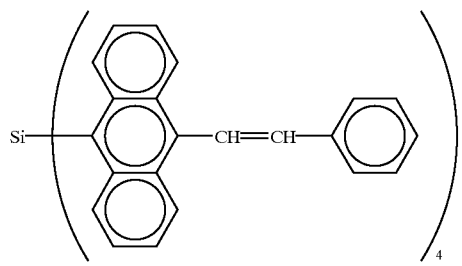
(3-10)
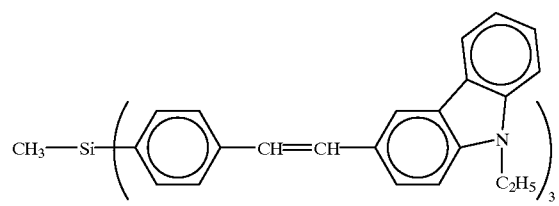
(3-11)
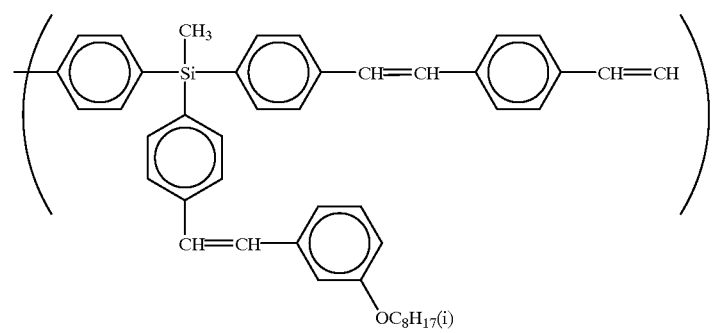
Mw = 7600 (converted to a polystyrene basis)
(3-12)
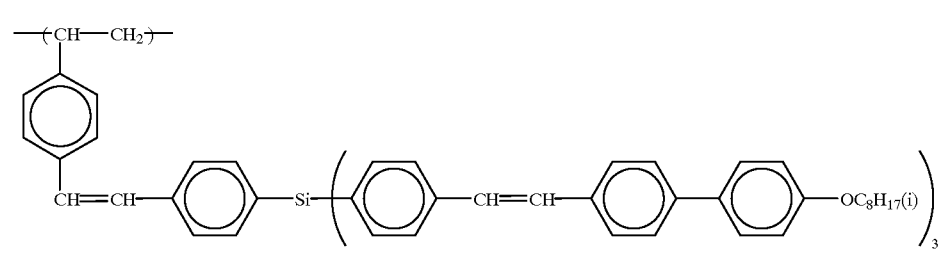
Mw = 13700 (converted to a polystyrene basis)
(3-13)
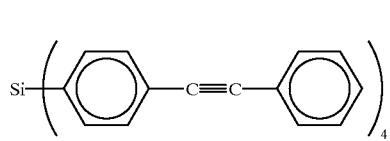
(4-1)
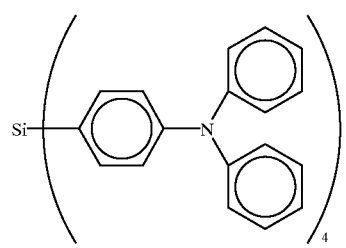

(4-2) 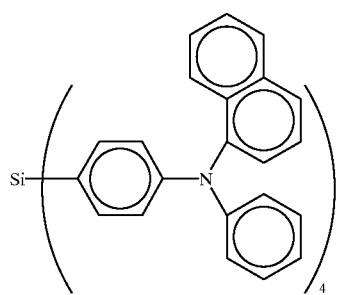
(4-3) 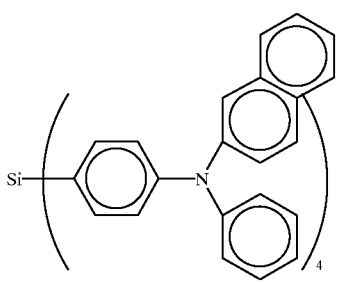
(4-4) 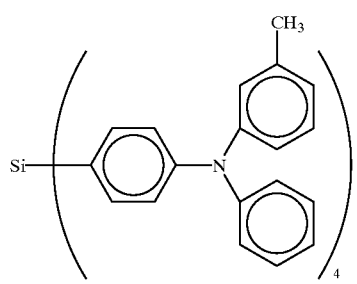
(4-5) 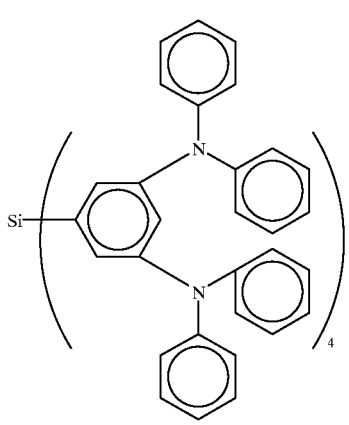
(4-6) 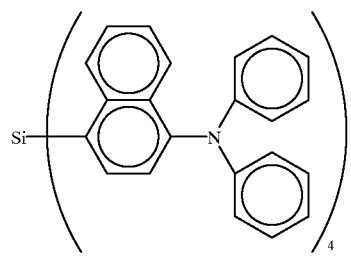
(4-7) 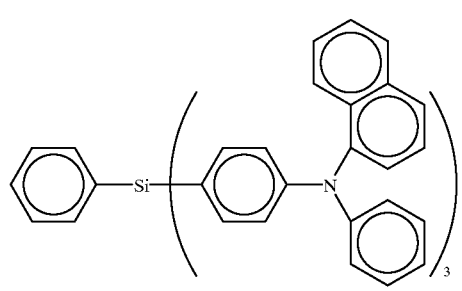
(4-8) 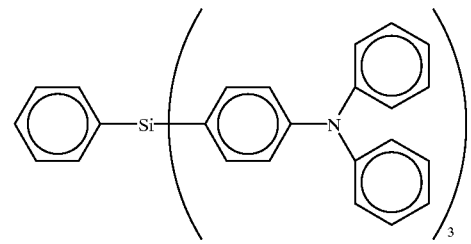
(4-9) 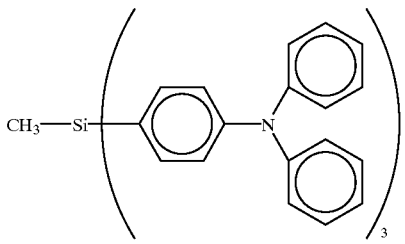

(4-10) (4-11)
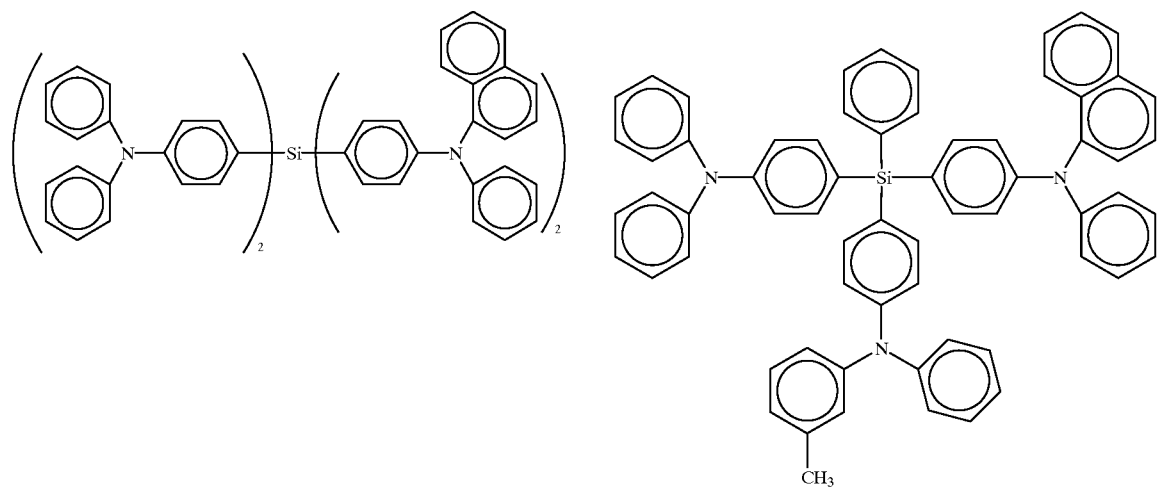
(4-12) (4-13)
(4-14) (4-15)
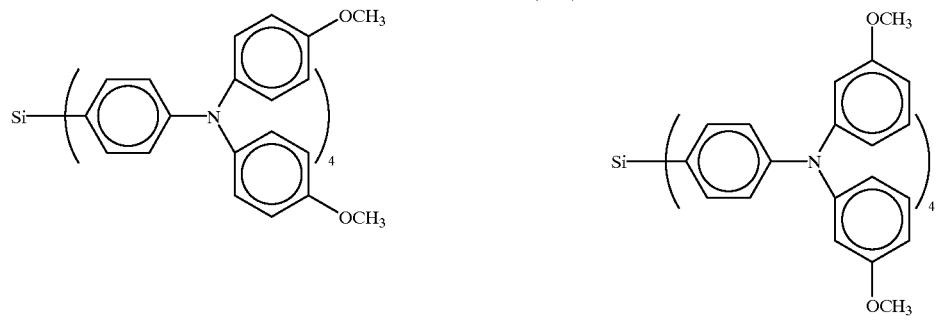
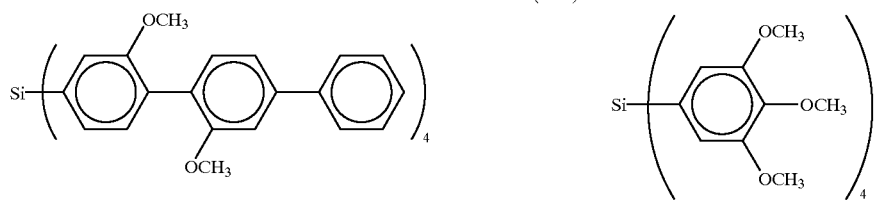
(4-16) (4-17)
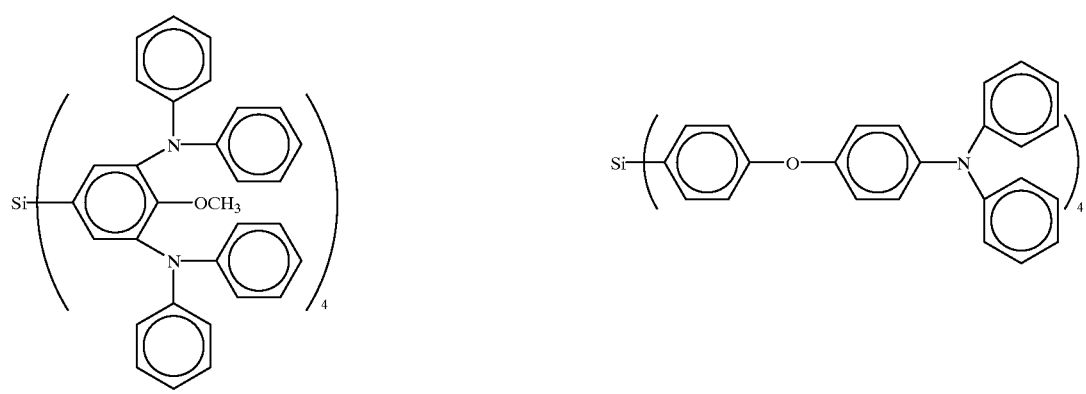

-continued
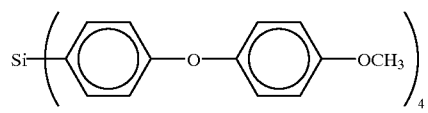 (4-18)
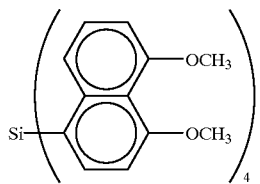 (4-19)
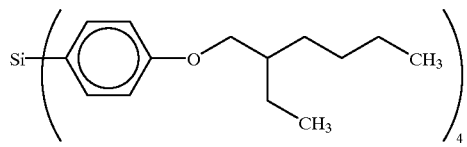 (4-20)
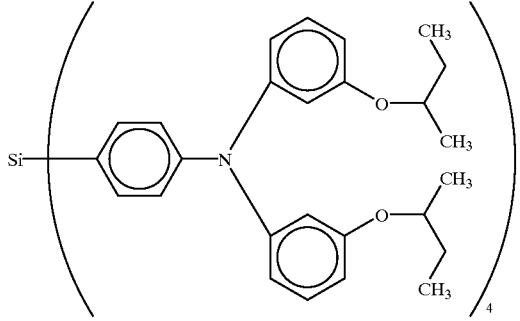 (4-21)
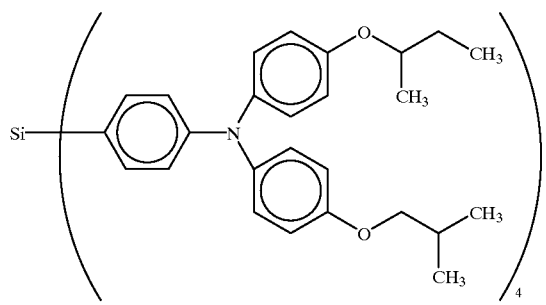 (4-22)
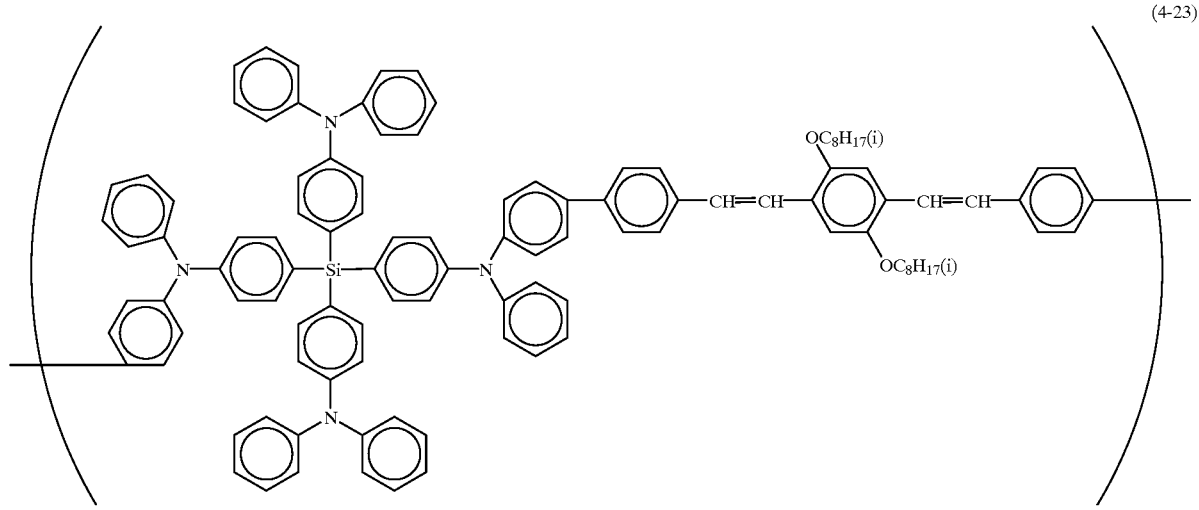 (4-23)
Mw = 8800 (converted to a polystyrene basis)

-continued
(4-24)
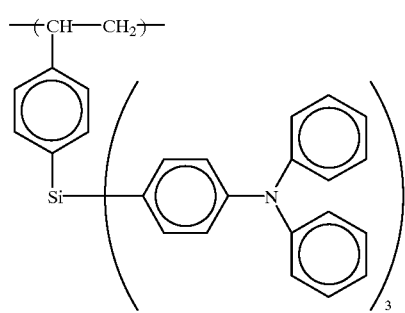
Mw = 10200 (converted to a polystyrene basis)
(4-25)
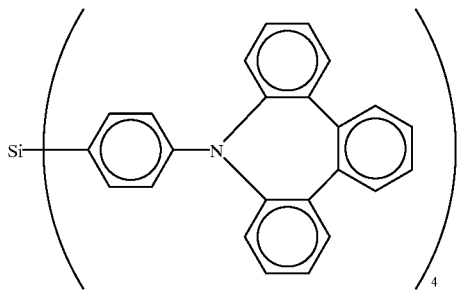
(4-26)
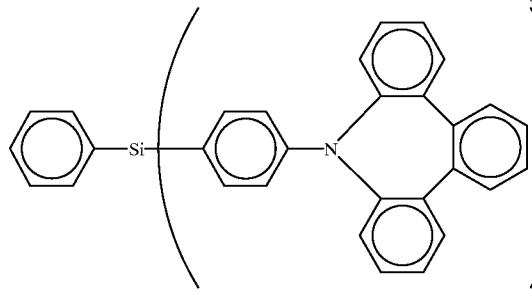
(4-27)
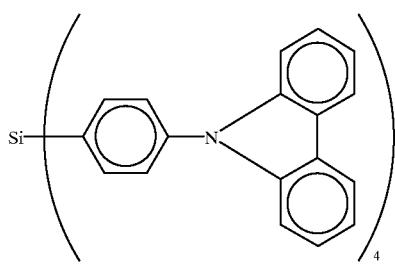
(4-28)
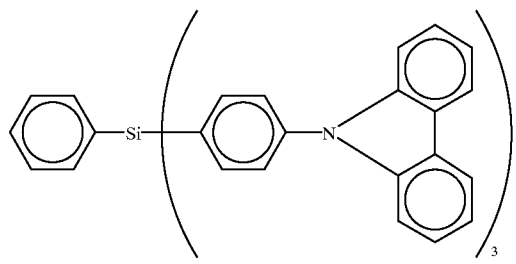
(4-29)
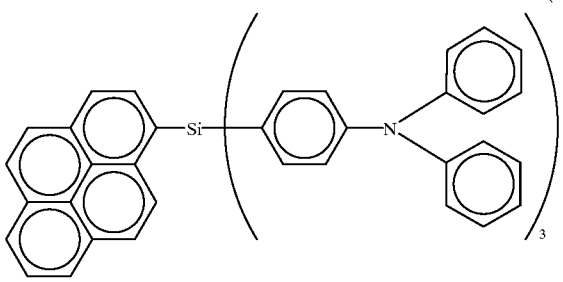
(4-30)
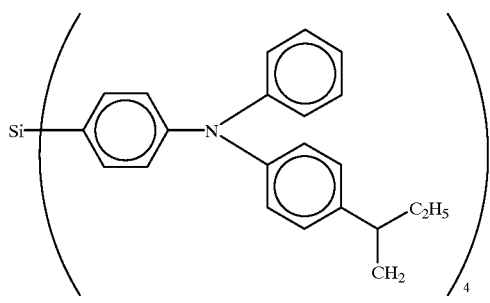
(4-31)
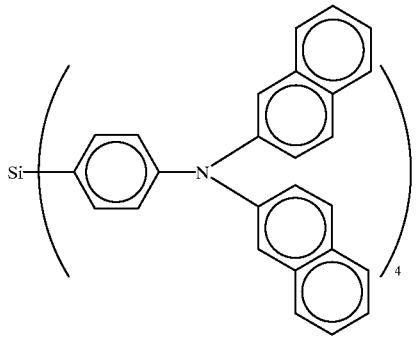

(4-32) 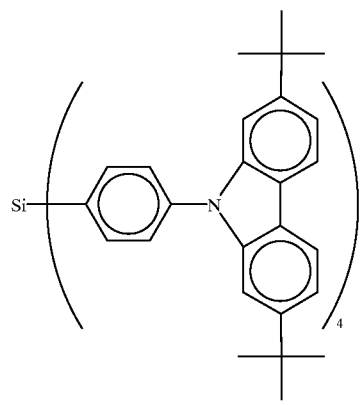
(4-33) 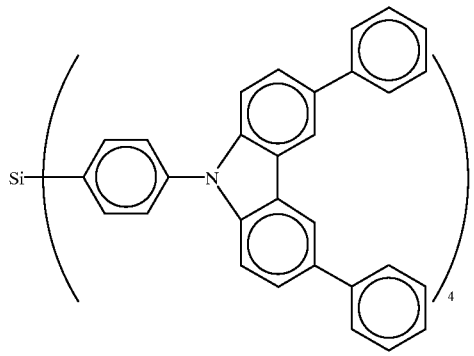
(4-34) 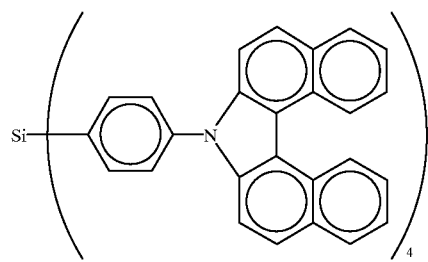
(4-35) 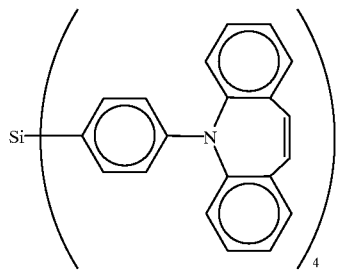
(5-1) 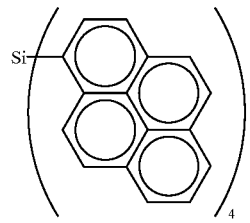
(5-2) 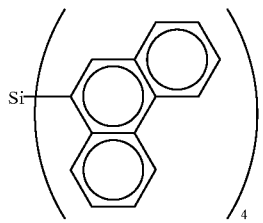
(5-3) 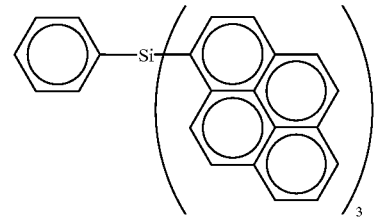
(5-4) 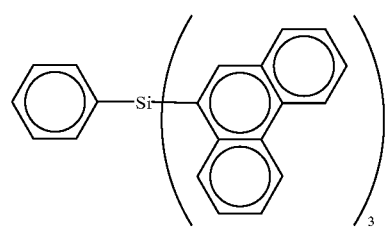
(5-5) 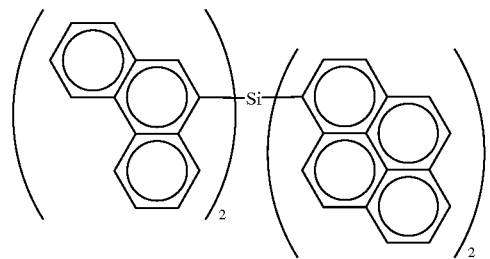
(5-6) 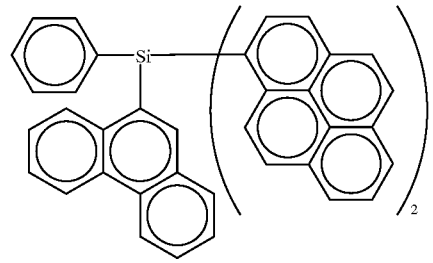

(5-7)

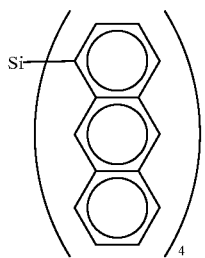

(5-8)

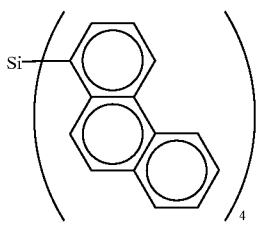

Methods of synthesizing the silane compounds of the present invention are illustrated below. From the viewpoint of their easy syntheses, it is undesirable that the compounds of the present invention have a spiro-structure containing a silicon atom as the spiro-atom.

The compounds of the present invention can be synthesized using various known methods. For instance, they can be synthesized by allowing lithioaryl derivatives (e.g., phenyllithium) to react with halogenated silicon compounds. For the formation of $Ar^{2i}$—$R^{2i}$, $Ar^{3i}$—$R^{3i}$ and $Ar^{4i}$—$R^{4i}$ bonds (i=1, 2 or 3) in the compounds of the present invention, it is advantageous to adopt the process of converting their respective precursors —$Ar^{2i}$—X, —$Ar^{3i}$—X and —$Ar^{4i}$—X (X=Cl, Br, I, —$OSO_2CH_3$ or —$OSO_2CF_3$, preferably Br or I) in the presence of a metallic catalyst according to various method (e.g., Suzuki coupling method using alkylboric acid derivatives, Heck reaction using alkene derivatives, Ullmann type reaction using amine derivatives, Still reaction using organotin compounds).

There is no particular restriction on the metallic catalyst used in the foregoing process, but copper and palladium derivatives, especially palladium derivatives, are used to advantage. The palladium catalysts have no particular limitations on their valence number and ligands Suitable examples of a palladium catalyst include palladium tetrakistriphenvlphosphine, palladium carbon, palladium dichloride dppf (wherein "dppf" stants for 1,1-bis-diphenylphosphinoferrocene), and palladium acetate.

For the reaction utilizing the palladium catalyst as described above, it is advantageous to use a base. The base has no particular restriction as to its species, but any of conventional bases, e.g., sodium carbonate, sodium acetate, rubidium carbonate and triethylamine, can be used. The amount of base used is not particularly limited, but it is desirable that the base be used in an amount of 0.1 to 20 equivalents, especially 1 to 10 equivalents, to the halide.

It is also advantageous to use a solvent for the reaction utilizing the palladium catalyst as described above. Such a solvent is not limited to particular compounds, but conventional ones, e.g., ethanol, water, ethylene glycol dimethyl ether, diethylene glycol dimethyl ether, dimethyl formamide, toluene, tetrahydrofuran, acetone and a mixture of two or more of the solvents described above, can be used.

Then, the luminescent devices comprising compounds according to the present invention are illustrated below. It does not matter what system, operation method and utilization form are applied to the luminescent devices of the present invention as long as the luminescent devices of the present invention utilize the silane compounds of the present invention. However, the luminescent devices utilizing luminescence from the compounds of the present invention and those using the compounds of the present invention as electric charge transfer materials are desirable. One of the representatives of luminescent devices is an organic electroluminescent (EL) device.

The organic layers of an organic luminescent device comprising any of the silane compounds of the present invention have no particular restrictions as to the formation method. Various methods, such as a resistance heating-utilized vapor deposition method, an electron-beam method, a sputtering method, a molecular lamination method, a coating method, an ink-jet method and a printing method can be adopted. In particular, the resistance heating-utilized vapor deposition method and the coating method are advantageous methods from the viewpoint of the production efficiency.

Every luminescent device of the present invention is a device having a luminescent layer or at least two thin layers of organic compounds, including a luminescent layer, between a pair of electrodes, an anode and a cathode. The thin layers which the device may have in addition to the luminescent layer are, e.g., a hole injection layer, a hole transfer layer, an electron injection layer, an electron transfer layer and a protective layer. The aforementioned layers each may have another function also. For forming each layer, various materials can be employed The anode supplies holes to a hole injection layer, a hole transfer layer and a luminescent layer. As a material for the anode, metals, alloys, metal oxides, electrically conductive compounds and mixtures thereof, preferably materials having a work function of at least 4 eV, can be used. Examples of such materials include conductive metal oxides, such as tin oxide, zinc oxide, indium oxide and indium tin oxide (ITO), metals such as gold, silver, chromium and nickel, mixtures or laminates of those metals and conductive metal oxides, inorganic conductive substances such as copper iodide and copper sulfide, organic conductive materials such as polyaniline, polylthiophene and polypyrrole, and laminates of those materials and ITO. Of the materials described above, the conductive metal oxides, especially ITO, are favored over the others from the viewpoint of productivity, conductivity and transparency. The suitable thickness of the anode, though can be selected depending on the anode material, is generally from 10 nm to 5 µm, more preferably 50 nm to 1 µm, further preferably 100 nm to 500 nm.

The anode has on a soda lime glass, alkali-free glass or transparent resin substrate an anode material formed into a layer. In a case of using a glass substrate, alkali-free glass is preferred from the viewpoint of reduction in ions eluted from the glass. When soda lime glass is used as the substrate, it is desirable that the barrier coat, such as silica, be provided on the glass. The thickness of the substrate has no particular limitation as long as the substrate can ensure mechanical strength. For instance, the suitable thickness of a glass substrate is at least 0.2 mm, preferably at least 0.7 mm.

The methods suitable for making the anode vary with the material used. In the case of ITO, for example, the film formation can be carried out using an electron-beam method, a sputtering method, a resistance heating-utilized vapor deposition method, a chemical reaction method (e.g., sol-gel method) orthemethodof coating a dispersion of indiumtinoxide. Washing and other treatments for the anode enable the device to get a reduction in driving potential and improve in light-emitting efficiency. In the case of an anode using ITO, it is effective for the anode to receive UV-ozone treatment or plasma treatment.

The cathode supplies electrons to an electron injection layer, an electron transfer layer and a luminescent layer. In selecting the cathode, the adhesiveness to the electron injection, electron transfer or luminescent layer adjacent to the cathode, the ionization potential and the stability are taken into consideration. As a material for the cathode, metals, alloys, metal halides, metal oxides, electrically conductive compounds and mixtures thereof can be employed. Examples of such materials include alkali metals (e.g., Li, Na, K), the fluorides thereof and the oxides thereof, alkaline earth metals (e.g., Mg, Ca), the fluorides thereof and the oxides thereof, gold, silver, lead, aluminum, Na—K alloy or a mixture thereof, Li—Al alloy or a mixture of Li—Al alloy and other metals, Mg—Ag alloy or a mixture of Mg—Ag alloy and other metals, and rare earth metals (e.g., In, Yb). Of these materials, the materials having a work function of at most 4 eV are preferred over the others. In particular, aluminum, Li—Al alloy or a mixture of Li—Al alloy and other metals and Mg—Ag alloy or a mixture of Mg—Ag alloy and other metals are used to advantage. The cathode structure may be a single-layer of the compound or mixture as described above or a lamination comprised of the compounds or mixtures as described above. The suitable thickness of the cathode, though can be selected depending on the cathode material, is generally from 10.nm to 5 μm, more preferably 50 nm to 1 μm, further preferably 100 nm to 1 μm.

In forming the cathode, various known methods, such as an electron-beam method, a sputtering method, a resistance heating-utilized vapor deposition method and a coating method, can be adopted. The metals as described above may be evaporated independently, or two or more thereof may be evaporated simultaneously. Further, it is possible to evaporate a plurality of metals at the same time to form an alloy electrode, or to evaporate the previously prepared alloy. It is advantageous to the luminescent device that both anode and cathode have low sheet resistance, specifically not higher than several hundreds Ω/□.

The material usable for a luminescent layer may be any of materials capable of forming a layer which can function so as to receive both hole injection from the anode, the hole injection layer or the hole transfer layer and electron injection from the cathode, the electron injection layer or the electron transfer layer when the electric field is applied thereto, permit the charges injected therein to move and enable the emission of light by providing a place for recombining the holes and the electrons. In a preferred embodiment of the present invention, the luminescent layer contains the silane compound(s) of the present invention. In addition, other materials hitherto known to be luminescent, such as benzoxazole derivatives, benzimidazole derivatives, benzothiazole derivatives, styrylbenzene derivatives, polyphenyl derivatives, diphenylbutadiene derivatives, tetraphenylbutadiene derivatives, naphthalimide derivatives, coumarin derivatives, perylene derivatives, perinone derivatives, oxadiazole derivatives, aldazine derivatives, pyraridine derivatives, cyclopentadiene derivatives, bis-styrylanthracene derivatives, quinacridone derivatives, pyrrolopyridine derivatives, thiadiazolopyridine derivatives, styrylamine derivatives, aromatic dimethylidyne derivatives, various metal complexes represented by metal complexes of 8-quinolinol, rare earth metal complexes or transition metal complexes (for example, orthometallized complexes such as tris(2-phenylpyridine)iridium(III) complex), and polymeric compounds such as polythiophene, polyphenylene and polyphenylenevinylene, may also be used in the luminescent layer. Although the luminescent layer has no particular restrictions as to the thickness, the suitable thickness thereof is generally from 1 nm to 5 μm, more preferably 5 nm to 1 μm, further preferably 10 nm to 500 nm.

As to the method of forming the luminescent layer, there is no particular restrictions, but various methods including a resistance heating-utilized vapor deposition method, an electron-beam method, a sputtering method, a molecular lamination method, a coating method (e.g., a spin coating, cast coating or dip coating method), an LB method, an ink-jet method and a printing method can be adopted. Of these methods, resistance heating-utilized vapor deposition and coating methods are preferred over the others.

The materials for the hole injection layer and the hole transfer layer may be any materials so long as they have any one of the functions as an injector of the holes from the anode, a transferor of holes and a barrier against electrons injected from the cathode. Examples of a material having one of such functions include carbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidyne compounds, porphyrin compounds, polysilane compounds, poly(N-vinylcarbazole) derivatives, aniline copolymers, thiophene oligomers, and conductive polymers represented by polythiophene, and the silane compounds of the present invention. The thickness of the hole injection layer and the hole transfer layer each, though it has no particular limitation, is generally from 1 nm to 5 μm, more preferably 5 nm to 1 μm, further preferably 10 nm to 500 nm. Each of the hole injection layer and the hole transfer layer may have a single-layer structure constituted of one or more of the materials described above or a multiple-layer structure made up of at least two layers having the same composition or different compositions.

As a method of forming a hole injection layer and a hole transfer layer, a vacuum evaporation method, an LB method, a method of coating a compound capable of injecting or transferring holes as described above in the form of a solution or dispersion in an appropriate solvent (using, e.g., a spin coating, cast coating or dip coating method), an ink-jet method and a printing method can be adopted. Examples of the solvent include a halogen-series solvent (e.g., chloroform, dichloroethane, etc.), water, an ether-series solvent (e.g., diethyl ether, tetrahydrofuran, etc.), an alcohol-series solvent (e.g., methanol, isopropanol, etc.), an ester-series solvent (e.g., ethyl acetate), a ketone-series solvent (e.g., acetone, etc.), a carboxylic acid-series solvent (e.g., acetic acid, etc.) and a mixture thereof. In the case of a coating method, the compound can be dissolved or dispersed in the presence of a resin component. Examples of a resin component usable therein include polyvinyl chloride, polycarbonate, polystyrene, polymethyl methacrylate, polybutyl methacrylate, polyester, polysulfone, polyphenylene oxide, polybutadiene, poly(N-vinylcarbazole), hydrocarbon resin, ketone resin, phenoxy resirn, polyamide, ethyl cellulose, polyvinyl acetate, ABS resin, polyurethane, melamine resin, unsaturatedpolyester resin, alkyd resin, epoxy resin and silicone resin.

The materials for the electron injection layer and the electron transfer layer may be any materials so long as they have any one of the functions as an injector of the electrons from the cathode, a transferor of electrons and a barrier against holes injected from the anode. Examples of a compound having such a function include triazole derivatives, oxazole derivatives, oxadiazole derivatives, fluorenone derivatives, anthraquinodimethane derivatives, anthrone derivatives, diphenylquinone derivatives, thiopyran dioxide derivatives, carbodimide derivatives, fluorenylidenemethane derivatives, distyrylpyrazine derivatives, tetracarboxylic acid anhydrides of aromatic condensed rings such as naphthalene and perylene, phthalocyanine derivatives, various metal complexes represented by metal complexes of 8-quinolinol derivatives, metallophthalocyanine and metal complexes containing benzoxazole or benzothiazole as a ligand, and silane compounds of the present invention. The thickness of the electron injection layer and the electron transfer layer each, though it has no particular limitation, is generally from 1 nm to 5 $\mu$m, more preferably 5 nm to 1 $\mu$m, further preferably 10 nm to 500 nm. Each of the electron injection layer and the electron transfer layer may have a single-layer structure constituted of one or more of the compounds as described above, or a multiple-layer structure made up of at least two layers having the same composition or different compositions.

As a method of forming the electron injection layer and the electron transfer layer, a vacuum evaporation method, an LB method, a method of coating the compound(s) capable of injecting or transferring electrons as described above in the form of a solution or dispersion in an appropriate solvent (using, e.g., a spin coating, cast coating or dip coating method), an ink-jet method and a printing method can be adopted. Examples of the solvent include a halogen-series solvent (e.g., chloroform, dichloroethane, etc.), water, an ether-series solvent (e.g., diethyl ether, tetrahydrofuran, etc.), an alcohol-series solvent (e.g., methanol, isopropanol, etc.), an ester-series solvent (e.g., ethyl acetate), a ketone-series solvent (e.g., acetone, etc.), acarboxylic acid-series solvent (e.g., acetic acid, etc.) and a mixture thereof. In a case of adopting the coating method, the electron-injecting or transferring compounds can be dissolved or dispersed in the presence of a resin component. Examples of a resin component usable therein include the same resins as employed for the hole injection and transfer layers.

The materials for a protective layer may be any substances so long as they have a function capable of inhibiting the invasion of a device deterioration promoter, such as moisture or oxygen, into the. device. Examples of such a substance include metals, such as In, Sn, Pb, Au, Cu, Ag, Al, Ti and Ni; metal oxides, such as MgO, SiO, $SiO_2$, $Al_2O_3$, GeO, NiO, CaO, BaO, $Fe_2O_3$, $Y_2O_3$ and $TiO_2$; metal fluorides, such as $MgF_2$, LiF, $AlF_3$ and $CaF_2$; polyethylene, polypropylene, polymethyl methacrylate, polyimide, polyurea, polytetrafluoroethylene, polychlorotrifluoroethylene, polydichlorodifluoroethylene, copolymer of chlorotrifluoroethylene and dichlorodifluoroethylene, copolymers prepared by polymerizing a mixture of tetrafluoroethylene and at least one comonomer, and fluorine-containing copolymers having cyclic structures on the main chain; a water-absorbing substance having a water absorption rate of at least 1%; and a moistureproof substance having a water absorption rate of at most 0.1%.

The protective layer also has no particular restriction as to the formation method, but any of a vacuum evaporation method, a sputtering method, a reactive sputtering method, a molecular beam epitaxy (MBE) method, a cluster ion beam method, an ion plating method, a plasma polymerization method (high frequency excitation ion plating method), a plasma chemical vapor deposition (CVD) method, a laser CVD method, a heat CVD method, a gas source CVD method and a coating method can be adopted for the formation thereof.

The present invention will now be illustrated in more detail by reference to the following examples. However, the invention should not be construed as being limited to these examples.

SYNTHESIS EXAMPLES

Synthesis of Compound (4-25):

Xylene in a volume of 50 ml was added to a mixture of 1 g of Compound a, 1.64 g of benzoazepine (Compound b), 0.74 g of t-BuONa, 0.01 g of $Pd(OAc)_2$ and 0.01 g of $P(t-Bu)_3$, and refluxed with stirring for 3 hours in an atmosphere of nitrogen. The resultant reaction solution was cooled to room temperature, and thereto were added 200 ml of chloroform and 200 ml of water. The organic layer thus separated was taken out, and concentrated. The concentrate obtained was purified by column chromatography on silica gel (developer: chloroform solvent), and then recrystallized from a chloroform/methanol mixture to yield 1.5 g of the desired Compound (4-25) as a white solid.

Synthesis of Compound (4-25)

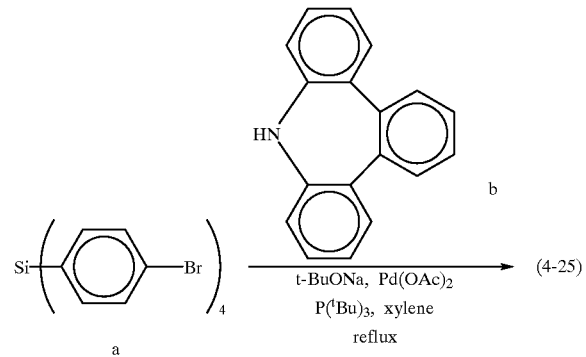

Synthesis of Compound (4-27)

The desired Compound (4-27) was synthesized as a white solid in an amount of 1.3 g in the same manner as in the synthesis of Compound (4-25), except that carbazole and $Rb_2CO_3$ were used in place of Compound b and t-BuONa respectively.

Synthesis of Compound (4-27)

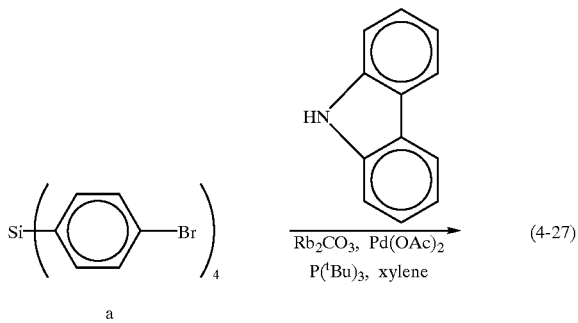

Synthesis of Compound (5-1)

Dehydrated ether in a volume of 100 ml was added to 5 g of Compound d, and stirred at room temperature in an atmosphere of nitrogen. Thereto, 10 ml of a 1.6M hexane solution of n-BuLi was added dropwise, and stirred for 10 minutes at room temperature. Further thereto, 0.41 ml of $SiCl_4$ was added dropwise, and stirred for 1 hour at room temperature. The resultant reaction solution was admixed with 300 ml of chloroform and 200 ml of water, and the organic layer separated therefrom was dried and then concentrated. The concentrate obtained was recrystallized from a chloroform/methanol mixture to yield 1.9 g of the desired Compound (5-1) as a light yellow solid.

Synthesis of Compound (5-1)

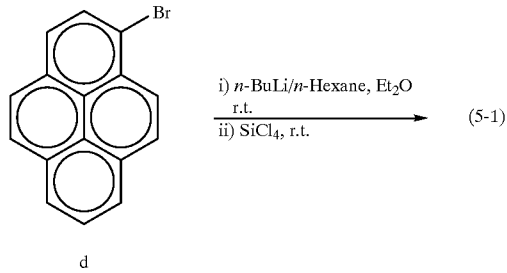

COMPARATIVE EXAMPLE 1

In 2 ml of dichloroethane, 40 mg of poly(N-vinylcarbazole), 12 mg of 2-t-butylphenyl-4-biphenyl-1,3,4-oxadiazole (PBD) and 1 mg of the following Compound A were dissolved. The solution prepared was spin-coated on an ITO substrate having undergone cleaning treatment, thereby forming a thin film about 130 nm in thickness. Then, a patterned mask (for adjusting each emission area to 5 mm×5 mm) was set on the organic thin film formed, and further thereon, inside the vacuum evaporator, Mg and Ag were deposited simultaneously in a Mg/Ag ratio of 10/1 to form a metallic film having a thickness of 50 nm, followed by deposition of a 50 nm-thick Ag film.

The thus produced electroluminescent (EL) device was made to luminesce by applying thereto a DC constant voltage by means of a source measure unit, Model 2400, made by Toyo Technica Co., Ltd. And the luminance and the wavelength of the luminescence which the device showed were measured using a luminometer BM-8, made by Topcon Co., and a spectrum analyzer PMA-11, made by Hamamatsu Photonics Co., respectively. As a result of these measurements, the luminescence the EL device gave off was found to be blue luminescence having the EL. at 470 nm and the luminance of 152 $cd/m^2$ under an operating voltage of 19 V. And this blue luminescence had color purity of (0.18, 0.20), expressed in the CIE chromaticity coordinates (x, y).

Compound A (Compound disclosed in JP-A-11-3781)

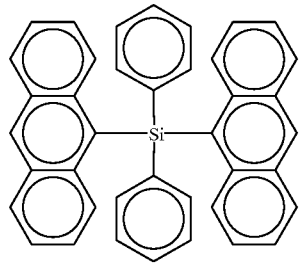

COMPARATIVE EXAMPLE 2

An ITO substrate which had undergone cleaning treatment was placed in an vacuum evaporator, and thereonto a TPD (N,N'-diphenyl-N,N'-di(m-tolyl)benzidine) was evaporated to form a film having a thickness of 40 nm, and further thereonto an Alq (tris(8-hydroxyquinolinato)aluminum complex) was evaporated to form a film having a thickness of 60 nm. Then, a patterned mask (for adjusting each emission area to 5 mm×5 mm) was set on those organic thin films and, further thereon, inside the vacuum evaporator, Mg and Ag were deposited simultaneously in a Mg/Ag ratio of 10/1 to form a metallic film having a thickness of 50 nm, followed by deposition of a 50 nm-thick Ag film.

The thus produced EL device was examined using the same method as in Comparative Example 1, and confirmed to show green luminescence. Thereafter, the EL device was allowed to stand for 5 hours, and examined again. As a result, the generation of many dark spots in the device was confirmed by visual observation.

COMPARATIVE EXAMPLE 3

An ITO substrate which had undergone cleaning treatment was placed in an vacuum evaporator, and thereonto a 40 nm-thick TPD (N,N'-diphenyl-N,N'-di(m-tolyl)benzidine) film, a 20 nm-thick film of Compound B illustrated below and a 40 nm-thick Alq (tris(8-hydroxyquinolinato)aluminum complex) film were evaporated sequentially in order of mention. Thereafter, the cathode was deposited thereon in the same manner as in Comparative Example 2.

The thus produced EL device was examined using the same method as in Comparative Example 1, and confirmed to show blue luminescence. Thereafter, the EL device was allowed to stand for one day. As a result, the dielectric breakdown was caused in the device to quench the luminescence.

Compound B (Compound disclosed in JP-A-11-3781)

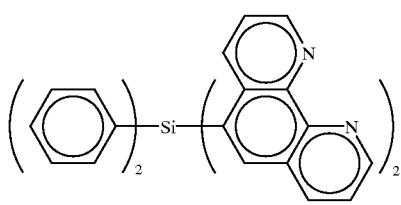

COMPARATIVE EXAMPLE 4

An EL device was produced in the same manner as in Comparative Example 2, except that Compound C illustrated below was used as hole transfer material, instead of TPD. The thus produced device was confirmed to exhibit green luminescence by the same examination as in Comparative Example 1. Thereafter, the EL device was allowed to stand for two days, and examined again. As a result, it was found that the dielectric breakdown was caused in the device.

Compound C (Compound disclosed in JP-A-10-265773)

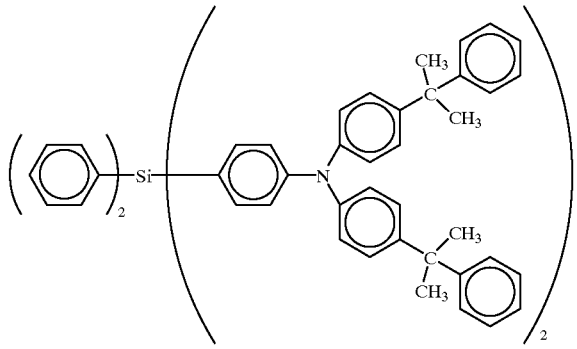

COMPARATIVE EXAMPLE 5

A cleaned substrate was placed in an evaporator. Onto this substrate, α-NPD (N,N'-di(1-naphthy)-N,N'-diphenylbenzidine) was evaporated in a thickness of 40 nm, then Compound A was evaporated in a thickness of 20 mm, and further Compound D was evaporated in a thickness of 40 nm. Furthermore, the cathode was deposited in the same manner as in Comparative Example 1. The thus produced device was evaluated by the same method as in Comparative Example 1. As a result, the device was found to merely give off faint blue luminescence.

Compound D

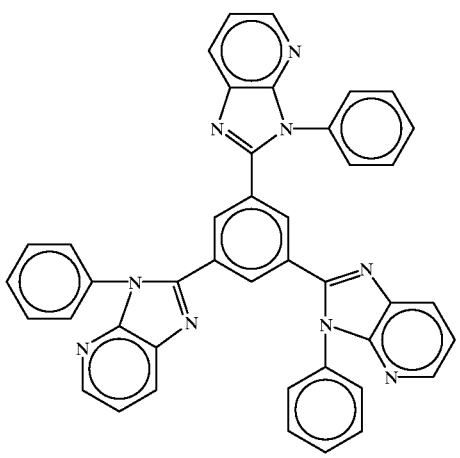

COMPARATIVE EXAMPLE 6

A cleaned substrate was placed in an evaporator. Onto this substrate, A-NPD was evaporated in a thickness of 40 nm first, and then Alq was evaporated in a thickness of 60 nm.

Further, the cathode was deposited in the same manner as in Comparative Example 1. The thus produced device was evaluated by the same method as in Comparative Example 1. As a result, the device was found to give off luminescence having the luminance of 5520 cd/m$^2$. Thereafter, the device was allowed to stand for 2 hours in an atmosphere of nitrogen under a temperature o f 100° C., and evaluated again. Therein, the generation of short-circuits in the device was observed.

EXAMPLE 1

In 2 ml of dichloroethane, 40 mg of poly (N-vinylcarbazole), 12 mg of 2-t-butylphenyl-4-biphenyl-1, 3,4-oxadiazole (PBD) and 1 mg of the Compound (2-1) of the present invention were dissolved. The solution prepared was spin-coated on an ITO substrate having undergone cleaning treatment, thereby forming a thin film about 130 nm in thickness. Then, a patterned mask (for adjusting each emission area to 5 mm×5 mm) was set on the organic thin film formed, and further thereon, inside the vacuum evaporator, Mg and Ag were deposited simultaneously in a Mg/Ag ratio of 10/1 to form a metallic film having a thickness of 50 nm, followed by deposition of a 50 nm-thick Ag film.

The thus produced electroluminescent (EL) device was made to luminesce by applying thereto a DC constant voltage by means of a source measure unit, Model 2400, made by Toyo Technica Co., Ltd. And the luminance and the wavelength of the luminescence the device showed were measured using a luminometer BM-8, made by Topcon Co. and a spectrum analyzer PMA-11, made by Hamamatsu Photonics Co., respectively. As a result of these measurements, the luminescence which the EL device gave off was found to be blue luminescence having the $EL_{max}$ at 418 nm and 437 nm and the luminance of 175 cd/m$^2$ under an operating voltage of 21 V. And this blue luminescence had good color purity of (0.17, 0.16), expressed in the CIE chromaticity coordinates (x, y).

The values on the CIE chromaticity coordinates are employed as an indication of color purity, and they signify that the color purity is better the smaller those values are. Therefore, the device of the present invention has proved to be superior in color purity to the EL device produced in Comparative Example 1.

EXAMPLE 2

An EL device was produced in the same manner as in Comparative Example 2, except that the Compound (4-1) of the present invention was used instead of TPD. The thus produced EL device was examined using the same method as in Comparative Example 1. Even after 5-hour standing, the dark-spot generation in the device was not detected by visual observation.

EXAMPLE 3

An EL device was produced in the same manner as in Comparative Example 3, except that the Compound (1-5) of the present invention was used instead of Compound B. The thus produced EL device was examined using the same method as in Comparative Example 1. Even after one-day standing, the device was confirmed showing blue luminescence.

EXAMPLE 4

A device was produced and evaluated in the same procedures as in Comparative Example 5, except that the Compound (2-19) of the present invention was used in place of Compound A. As a result, it was found that the device gave off blue luminescence having chromaticity coordinates of (0.19, 0.29), the maximum luminance of 4280 cd/m$^2$ and an external quantum efficiency of 1.09% in the vicinity of 100 cd/m$^2$.

EXAMPLE 5

A device was produced and evaluated in the same procedures as in Comparative Example 5, except that the Compound (5-1) of the present invention was used in place of Compound A. As a result, it was found that the device gave off blue luminescence having chromaticity coordinates of (0.18, 0.29), the maximum luminance of 4500 cd/m$^2$ and an external quantum efficiency of 1.32% in the vicinity of 100 cd/m$^2$.

EXAMPLE 6

A device was produced and evaluated in the same procedures as in Comparative Example 6, except that the Compound (4-25) of the present invention was used in place of α-NPD. As a result, the device gave off luminescence having a maximum luminance of 6540 cd/m$^2$. When the device was allowed to stand for 2 hours at 100° C. in an atmosphere of nitrogen and then evaluated again, the maximum luminance of the thus aged device was 5220 cd/m$^2$.

EXAMPLE 7

A device was produced and evaluated in the same procedures as in Comparative Example 6, except that the Compound (4-27) of the present invention was used in place of α-NPD. As a result, the device gave off luminescence having a maximum luminance of 4680 cd/m$^2$. When the device was allowed to stand for 2 hours at 100° C. in an atmosphere of nitrogen and then evaluated again, the maximum luminance of the thus aged device was 3190 cd/m$^2$.

In the same manner as the above, EL devices were produced using the other silane compounds according to the present invention respectively, and they each was examined by the same method as mentioned above. As a result, it was confirmed that the silane compounds of the present invention functioned as EL device materials. Further, it was found that the EL devices comprising the silane compounds of the present invention generated less dark spots and caused less short-circuits, namely they had excellent durability.

The silane compounds of the present invention are usable as materials for organic EL devices, and the devices comprising the compounds of the present invention can have excellent electroluminescent characteristics, including color hue, luminance and durability. Further, the compounds of the present invention are utilizable for medical supplies, brightening agents, photographic materials, UV absorbing materials, laser dyes, color filter dyes and color conversion filters.

While the invention has been described in detail and with reference to specific embodiments thereof, it will be apparent to one skilled in the art that various changes and modifications can be made therein without departing from the spirit and scope thereof.

What is claimed is:

1. A luminescent device material, said material comprising a compound represented by the following formula (1):

(1)

wherein $R^1$ represents an alkyl group, an aryl group, a heteroaryl group or an alkynyl group, and each of $Ar^{11}$, $Ar^{12}$ and $Ar^{13}$ represents a heteroaryl group.

2. A luminescent device material, said material comprising a compound represented by the following formula (2):

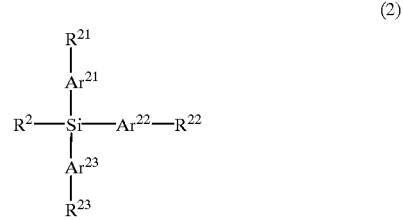

(2)

wherein $R^2$ represents an alkyl group, an aryl group, a heteroaryl group or an alkynyl group, each of $Ar^{21}$, $Ar^{22}$ and $Ar^{23}$ represents an arylene group , and each of $R^{21}$, $R^{22}$ and $R^{23}$ represents an aryl group or a heteroaryl group.

3. A luminescent device material, said material comprising a compound represented by the following formula (3):

(3)

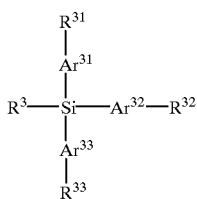

wherein $R^3$ represents an alkylgroup, an aryl group, aheteroaryl group or an alkynyl group, each of $Ar^{31}$, $Ar^{32}$ and $Ar^{33}$ represents an arylene group, and each of $R^{31}$, $R^{32}$ and $R^{33}$ represents an alkenyl group or an alkynyl group.

4. A luminescent device material, said material comprising a compound represented by the following formula (4):

(4)

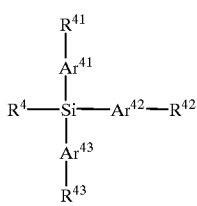

wherein $R^4$ represents an alkyl group, an aryl group, a heteroaryl group or an alkynyl group, each of $Ar^{41}$, $Ar^{42}$ and $Ar^{43}$ represents an arylene group, each of $R^{41}$, $R^{42}$ and $R^{43}$ represents $-NR^{44}R^{45}$, $-OR^{46}$ or $-S-R^{47}$, and each of $R^{44}$, $R^{45}$, $R^{46}$ and $R^{47}$ represents a hydrogen atom or a substituent group.

5. A luminescent device material, said material comprising a compound represented by the following formula (5):

(5)

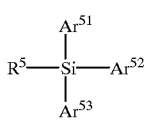

wherein $R^5$ represents an alkyl group, an aryl group, a heteroaryl group or an alkynyl group, and each of $Ar^{51}$, $Ar^{52}$ and $Ar^{53}$ represents a group containing at least three aromatic hydrocarbon rings in a condensed state.

6. A compound represented by the following formula (6):

(6)

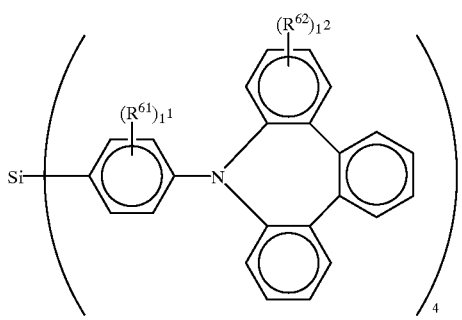

wherein each of $R^{61}$ and $R^{62}$ represents a substituent group, $l^1$ represents an integer of 0 to 4, and $l^2$ represents an integer of 0 to 12.

7. A compound represented by the following formula (7):

(7)

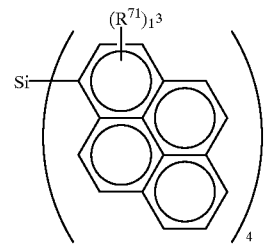

wherein $R^{71}$ represents a substituent group, and $l^3$ represents an integer of 0 to 9.

8. A compound represented by the following formula (8):

(8)

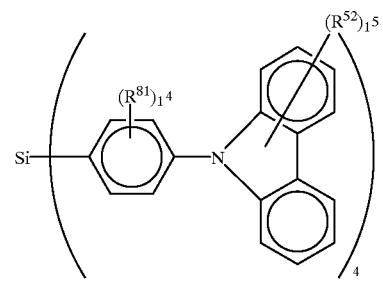

wherein each of $R^{81}$ and $R^{82}$ represents a substituent group, $l^4$ represents an integer of 0 to 4, and $l^5$ represents an integer of 0 to 8.

9. A luminescent device comprising at least one among the compounds represented by the formulae (1), (2), (3), (4), (5), (6), (7) and (8) claimed in claim 1, 2, 3, 4, 5, 6, 7 or 8 respectively.

10. The luminescent device material as claimed in claim 1, wherein $R^1$ represents an alkyl group, an aryl group or a heteroaryl group.

11. The luminescent device material as claimed in claim 1, wherein each of $Ar^{11}$, $Ar^{12}$ and $Ar^{13}$ represents a pyridyl group, a pyrazinyl group, an oxadiazolyl group, a triazolyl group, a thiadiazolyl group, a thienyl group, a carbazolyl group, a quinolino group, a benzazolyl group or a carbazolyl group.

12. The luminescent device material as claimed in claim 2, wherein $R^2$ represents an alkyl group, an aryl group or a heteroaryl group.

13. The luminescent device material as claimed in claim 2, wherein each of $Ar^{21}$, $Ar^{22}$ and $Ar^{23}$ represents a phenylene group, a naphthylene group, an anthrylene group, a pyrenylene group or a rubrenylene group.

14. The luminescent device material as claimed in claim 2, wherein each of $R^{21}$, $R^{22}$ and $R^{23}$ represents a heteroaryl group or a group containing at least three aromatic hydrocarbon rings in a condensed state.

15. The luminescent device material as claimed in claim 3, wherein $R^3$ represents an alkyl group, an aryl group or a heteroaryl group.

16. The luminescent device material as claimed in claim 3, wherein each of $Ar^{31}$, $Ar^{32}$ and $Ar^{33}$ represents a phenylene group, a naphthylene group, an anthrylene group, a pyrenylene group or a rubrenylene group.

17. The luminescent device material as claimed in claim 3, wherein each of $R^{31}$, $R^{32}$ and $R^{33}$ represents an alkenyl group or an alkynyl group.

18. The luminescent device material as claimed in claim 4, wherein $R^4$ represents an alkyl group, an aryl group or a heteroaryl group.

19. The luminescent device material as claimed in claim 4, wherein each of $Ar^{41}$, $Ar^{42}$ and $Ar^{43}$ represents a phenylene group, a naphthylene group, an anthrylene group, a pyrenylene group or a rubrenylene group.

20. The luminescent device material as claimed in claim 4, wherein each of $R^{41}$, $R^{42}$ and $R^{43}$ represents —$NR^{44}R^{45}$ or —$OR^{46}$.

* * * * *